(12) United States Patent
Huffaker et al.

(10) Patent No.: US 9,181,309 B1
(45) Date of Patent: Nov. 10, 2015

(54) PEPTIDE REGULATION OF MAIZE DEFENSE RESPONSES

(71) Applicant: The United States of America, as represented by the Secretary of Agriculture, Washington, DC (US)

(72) Inventors: Alisa Huffaker, Newberry, FL (US); Eric A Schmelz, Gainesville, FL (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 162 days.

(21) Appl. No.: 13/632,620

(22) Filed: Oct. 1, 2012

Related U.S. Application Data

(60) Provisional application No. 61/542,150, filed on Sep. 30, 2011.

(51) Int. Cl.
*C07K 14/415* (2006.01)
*C12N 15/82* (2006.01)

(52) U.S. Cl.
CPC .......... *C07K 14/415* (2013.01); *C12N 15/8282* (2013.01)

(58) Field of Classification Search
None
See application file for complete search history.

(56) References Cited

U.S. PATENT DOCUMENTS

2006/0141495 A1* 6/2006 Wu .................................. 435/6

* cited by examiner

*Primary Examiner* — Medina A Ibrahim
(74) *Attorney, Agent, or Firm* — John D. Fado; Howard V. Owens, Jr.; Gail E. Poulos

(57) ABSTRACT

Herein is identified a novel gene, ZmproPEP3, encoding a bioactive peptide, ZmPEP3, from *Zea mays*, wherein the peptide finds utility in regulating expression of both herbivory-defense regulating signals, herbivore and pathogen defense genes, production of defense-related metabolites, inducing broad antimicrobial activity and increasing plant volatiles.

11 Claims, 20 Drawing Sheets

```
gi 163965699|gb|AC209428.2|AC209428 HTG Zea mays chromosome 2 clone CH201-162E12; ZMMBBc0162E12,
***
            SEQUENCING IN PROGRESS ***, 21 unordered pieces.
        Length = 190320

Score = 85.1 bits (209), Expect = 6e-16
 Identities = 61/127 (48%), Positives = 69/127 (54%), Gaps = 19/127 (14%)
 Frame = +1

Query: 1      MAEVEASAPLFAHPFSLLQPLLRACACCIVGL-HGYCSDNNDSKPAAAATAESSTPQEGE 59
              + E +ASAPL        Q LLRACA C LVGL  GY SD   +  AAAA   - +PQEG+
Sbjct: 146065 VVEEQASAPL--------QLLLRACACCLVGLLRCYRSDPKPAAAAAAASVAAESPQECD 146220

Query: 60     AGGGGDD----------------DDKAAAYLYVQE-VATPVLAARR-PPTQFGPPEEGSG 101
                G                     D +    LYVQE V T VLAA R PP   P PPEEGSG
Sbjct: 146221 KPFGSVSVRGIRLIISPCCNP*MDVQPLRCLYVQDEVGTQVLAATRTPPWPFCPPEEGSG 146400

Query: 102    GEGGSHN 108    (SEQ ID NO: 8)
              G GGSHN
Sbjct: 146401 GNGGSHN 146421  (SEQ ID NO: 9)
```

FIG. 1

```
145,890: ACCAGGAATGGATCAGCGCGTCTCCCAGGAATCGTCGTCGGATCGTCGGCGCAAGCGCAA
                  M  D  Q  R  V  S  Q  E  S  S  S  D  R  R  R  K  R  K 145,950: AGACGTCGCGGCGGCGGTGCCGGAGGGCGTCCACGGAGAGTCCACGGACAACGGCGGGTA
          D  V  A  A  A  V  P  E  G  V  H  G  E  S  T  D  N  G  G  Y 146,010: CGACGATACTGATGAGACCGCGGGTGTGCTGACCAAGGAGCAGCAGGCGGTGGATGTGGT
          D  D  T  D  E  T  A  G  V  L  T  K  E  Q  Q  A  V  D  V  V 146,070: CGAAGAACAAGCCTCGGCGCCGCTCCAGCTCCTGCTCCGCGCCTGCGCCGGCTGCCTGGT
          E  E  Q  A  S  A  P  L  Q  L  L  L  R  A  C  A  G  C  L  V 146,130: GGGCCTTCTGCGCGGCTACCGCAGCGACCCGAAGCCGGCCGCCGCCGCCGCTGCTGCTTC
          G  L  L  R  G  Y  R  S  D  P  K  P  A  A  A  A  A  A  S 146,190: TGTGGCCGCAGAATCGCCGCAGGAAGGAGACAAGCCGTTTGGCAGC TAAGTGTTCGAGG
          V  A  A  E  S  P  Q  E  G  D  K  P  F  G  S 146,250: CCACCGCTTGATTATTTCTCCGTGCTGTAACCCGTAGATGGATGTGCAACCGTTGCGGTG 146,310: TCTGTACGTGCAGG GGAGGTGGGCACTCAGGTGTTGGCGGCGACGAGGACGCCGCCGTG
                        E  E  V  G  T  Q  V  L  A  A  T  R  T  P  P  W 146,370: GCCGCCGTGCCCTCCTGAAGAAGGTTCCGGTGGCAATGGAGGCAGCCACAACTAG  (SEQ ID NO: 10)
          P  P  C  P  P  E  E  G  S  G  G  N  G  G  S  H  N  *
```

FIG. 2

```
B73ZmproPEP3    MDQRVSQESSSDRRRKRKDVAAAVSEGVHGESTDNGGYDDTDETAGVLTKEQQAVDVVEE 60
Predicted       MDQRVSQESSSDRRRKRKDVAAAVPEGVHGESTDNGGYDDTDETAGVLTKEQQAVDVVEE 60
GQZmproPEP3     MDQRVSQESSSDRRRKRKDVAAAVPEGVHGESTDNGGYDDTDETAGVLTKEQQAADVVEE 60

B73ZmproPEP3    QASAPLQLLLRACAGCLVGLLHGYRSDPKPAAAAAAASVAAESPQEGDKPFGSEEVGTQV 120
Predicted       QASAPLQLLLRACAGCLVGLLRGYRSDPKPAAAAAAASVAAESPQEGDKPFGSEEVGTQV 120
GQZmproPEP3     EASSPLQLLLRACAGCLVGLLCGYRSDPKP-AAAAAASVAAESPQEGDKPFGSEEVGTQV 119

B73ZmproPEP3    LAATRTPPWPPCPPEEGSGGNGGSHN 146 (SEQ ID NO: 11)
Predicted       LAATRTPPWPPCPPEEGSGGNGGSHN 146 (SEQ ID NO: 12)
GQZmproPEP3     LAATRTPPWPPCPPEEGSGGNGGSHN 145 (SEQ ID NO: 13)
```

FIG. 3

| Antimicrobial/Antifungal Proteins | Biosynthetic Enzymes for Defensive Secondary Metabolites | Redox Signaling & Scavenging | Defense Signaling |
|---|---|---|---|
| Defensin | IGL3 – Volatile Indole | GST20 | ACC Oxidase – Ethylene |
| Endochitinase A | TPS1 – Nerolidol | GST25 | LOX – JA/Oxylipins |
| PR-4 | TPS11 – Macrocarpene | GSTIV | AOS – JA/Oxylipins |
| PR protein | TPS23 – Caryophyllene | Peroxidase | AOC – JA/Oxylipins |
| Thaumatin | PPO2 – Polymerization of phenolics | | OPR1 – JA/Oxylipins |
| Hevein | | | |

FIG. 6

| Substance | Amount (ng/g) Water | ZmPep3 | Fold Change |
|---|---|---|---|
| DMNT (dimethyl nonatriene) | 385.78 | 2,341.26 | 6.07 |
| beta-Caryophyllene | 8.13 | 1,295.11 | 159.26 |
| beta-Farnesene | 1.36 | 1,279.83 | 935.03 |
| Indole | 5.31 | 672.44 | 126.54 |
| 3-Hexenyl Acetate | 699.41 | 653.97 | 0.94 |
| beta-Linalool | 35.39 | 523.05 | 14.78 |
| Nerolidol | 0.79 | 286.17 | 364.54 |
| alpha-Bergamotene | 0.20 | 211.47 | 1050.6 |
| Trimethyl Tridecatetraene | 15.28 | 162.02 | 10.6 |
| beta-Ocimene | 6.92 | 59.20 | 8.47 |
| Humulene | 1.05 | 56.30 | 53.79 |
| beta-Myrcene | 4.25 | 35.41 | 8.34 |
| alpha-Farnesene | 2.29 | 28.86 | 12.58 |
| MeSA? | 4.25 | 18.30 | 4.31 |
| alpha-Limonene | 0.68 | 18.12 | 26.47 |
| Z3-Hexen-1-ol | 18.18 | 17.45 | 0.96 |
| cis-jasmone | 0.34 | 6.88 | 20.12 |
| beta-pinene | 0.44 | 1.71 | 3.86 |
| alpha-pinene | 0.83 | 0.99 | 1.2 |

FIG. 11

ZmPEP3-Induced metabolite synthetic blend

| Volatile | Media formulation |
|---|---|
| DMNT (dimethyl nonatriene) | 5.52 mM |
| beta-Caryophyllene | 2.2 mM |
| beta-Farnesene | 2.2 mM |
| Indole | 2 mM |
| 3-Hexenyl Acetate | 1.66 mM |
| beta-Linalool | 1.28 mM |
| Nerolidol | 0.46 mM |
| Humulene | 0.122 mM |
| beta-Myrcene | 0.092 mM |
| alpha-Farnesene | 0.05 mM |
| MeSA? | 0.042 mm |
| alpha-Limonene | 0.05 mm |
| Z3-Hexen-1-ol | 0.064 mM |

Wound-Induced metabolite synthetic blend

| Volatile | Media formulation |
|---|---|
| DMNT (dimethyl nonatriene) | 0.931 mM |
| beta-Caryophyllene | 0.014 mM |
| beta-Farnesene | 0.0023 mM |
| Indole | 0.16 mM |
| 3-Hexenyl Acetate | 1.75 mM |
| beta-Linalool | 0.081 mM |
| Nerolidol | 0.0012 mM |
| Humulene | 0.0017 mM |
| beta-Myrcene | 0.011 mM |
| alpha-Farnesene | 0.0038 mM |
| MeSA? | 0.010 mM |
| alpha-Limonene | 0.0017 mM |
| Z3-Hexen-1-ol | 0.065 mM |

PEPTIDE REGULATION OF MAIZE DEFENSE RESPONSES

RELATED APPLICATIONS

This application is claims priority to U.S. Provisional Patent Application Ser. No. 61/542,150, filed Sep. 30, 2011 the contents of which are incorporated herein by reference in their entirety.

FIELD OF THE INVENTION

The present invention relates to a peptide that can be used to modulate herbivore and pathogen defense responses in maize.

SUMMARY OF THE INVENTION

Herein is identified a novel gene, ZmproPEP3, encoding a bioactive peptide, ZmPEP3, from Zea mays.

Another embodiment is ZmPEP3, and homologs thereof, regulated expression of both herbivore and pathogen defense genes.

A further embodiment is ZmPEP3 regulated production of defense-related metabolites.

A further embodiment is ZmPEP3-induced metabolites with broad antimicrobial activity.

A further embodiment is ZmPEP3-induced metabolites that suppress aflatoxin production by A. flavus.

An additional embodiment is ZmPEP3-induced plant volatiles and herbivory defense.

BRIEF DESCRIPTION OF THE DRAWINGS

FIG. 1 is a query of the ZmproPEP3 gene (Sbjct) discovered by alignment with the previously identified ZmproPEP1 gene using the tBLASTN program.

FIG. 2 is a picture of the translation of the Z. mays Chromosome 2 BAC clone, GenBank Number AC209428, fragment encoding the ZmproPEP3 peptide precursor gene. Predicted exons are shown in black and the predicted intron is gray. The predicted 23 amino acid bioactive peptide sequence is designated by underlining.

FIG. 3 is a picture of the alignment of the protein sequences encoded by the cloned ZmproPEP3 genes from Z. mays var. B73 (B73ZmproPEP3) and Z. mays var. Golden Queen (GQZmproPEP3) with the predicted protein encoded on the GenBank accession AC209428 Z. mays Chromosome 2 BAC clone (Predicted). The predicted 23 amino acid bioactive peptide (in blue) is identical in all three sequences. Alignment was made using the CLUSTAL 2.0.11 multiple sequence alignment from EBI

FIG. 6 is a table of defense-related genes activated by ZmPEP3 treatment as ascertained by RT-PCR

FIG. 11 is a table listing the quantity of each measured defense metabolite emitted in leaves treated with water or with ZmPEP3.

FIG. 12 is a table of the media formulations used to generate synthetic blends mimicking water or ZmPEP3 induced metabolites for use in bioassays.

DESCRIPTION OF THE INVENTION

Figure 4:
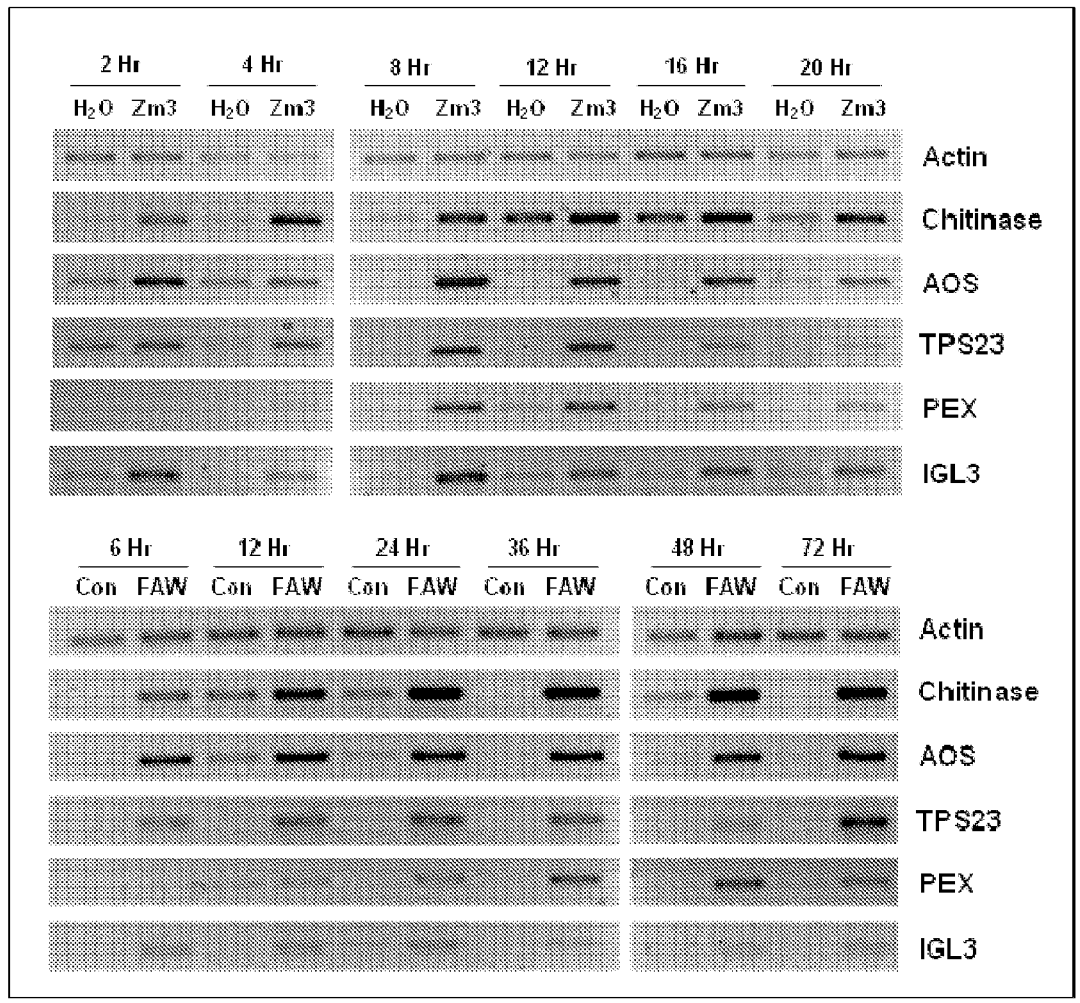
FIG. 4 is a photo of ZmPEP3 induced expression of herbivory defense genes. Semiquantitative RT-PCR analysis of transcript abundance for selected herbivory defense marker genes in leaves treated with ZmPep3 (upper panel) or subjected to herbivory by Spodoptera exigua (fall armyworm—FAW) (lower panel). Leaves were excised and treated with either water or ZmPEP3 over a 16 hour time course or subjected to herbivory for a 72 hour timecourse.
Figure 5:
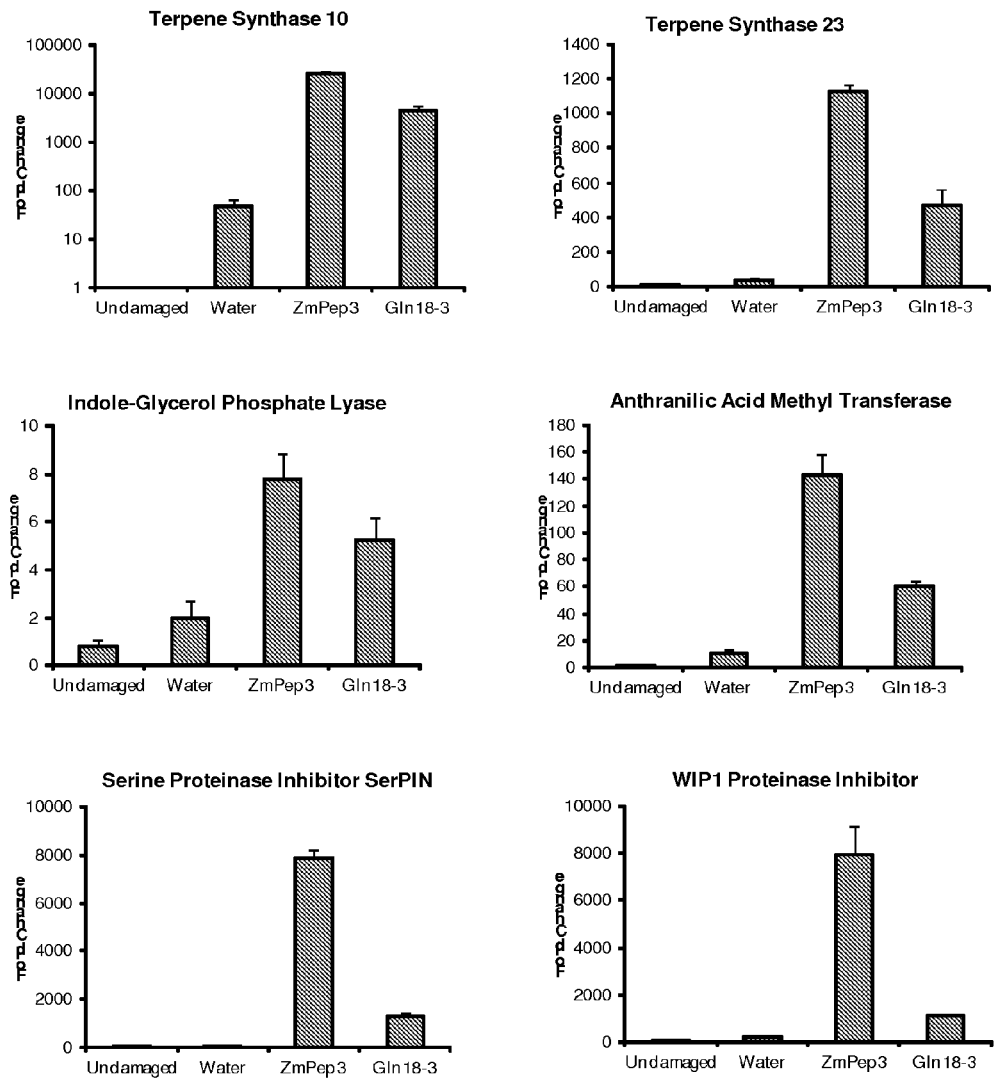
FIG. 5 represents graphs of expression of genes associated with both direct and indirect herbivore defenses induced by treatment with ZmPEP3 or with the insect elicitor of plant defense glutamine-linolenate (Gln-18:3) as analyzed by real time qPCR. Indole-Glycerol Phosphate Lyase, Anthranilic Acid Methyl Transferase and Terpene Synthases 10 and 23 encode enzymes that produce volatiles associated with indirect herbivore defense through attraction of natural enemy insects. The proteinase inhibitor genes, SerPIN and WIP1 encode proteins that have a direct antinutritive effect on caterpillar larvae.

The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurement.

A cell, tissue, organ, or organism into which has been introduced a foreign polynucleotide, such as a recombinant vector, is considered "transformed", "transfected", or "transgenic." A "transgenic" or "transformed" cell or organism also includes progeny of the cell or organism and progeny produced from a breeding program employing such a "transgenic" plant as a parent in a cross and exhibiting an altered phenotype resulting from the presence of a recombinant polynucleotide construct.

The term "plant" encompasses any higher plant and progeny thereof, including monocots, dicots, gymnosperms, and other plants and includes parts of plants, including reproductive units of a plant (e.g., seeds), fruit, flowers, etc.

Three and one-letter code for amino acids. For the polypeptide and peptide sequences presented herein, either the three-letter code or the one-letter code may be used for representing amino acid residues.

The ZmPeP3 peptide can be expressed in plants or plant cells under the control of an operably linked promoter that is capable of expression in the plant or plant cell. Any well-known method can be employed for plant cell transformation, culture, and regeneration in the practice of the present invention with regard to a particular plant species. Conventional methods for introduction of foreign DNA into plant cells include, but are not limited to: (1) *Agrobacterium*-mediated transformation (Lichtenstein and Fuller In: Genetic Engineering, Vol 6, Rigby, ed., London, Academic Press, 1987; and Lichtenstein and Draper, in: DNA Cloning, Vol II, Glover, ed., Oxford, IRI Press, 1985); (2) particle delivery (see, e.g., Gordon-Kamm et al., Plant Cell 2:603, 1990; or BioRad Technical Bulletin 1687), (3) microinjection (see, e.g., Green et al., Plant Tissue and Cell Culture, Academic Press, New York, 1987), (4) polyethylene glycol (PEG) procedures (see, e.g., Draper et al., Plant Cell Physiol. 23:451, 1982); Zhang and Wu, Theor. Appl. Genet. 76:835, 1988), (5) liposome-mediated DNA uptake (see, e.g., Freeman et al., Plant Cell Physiol. 25:1353, 1984), (6) electroporation (see, e.g., Fromm et al., Nature 319:791, 1986); and (7) vortexing method (see, e.g., Kindle, Proc. Natl. Acad. Sci. USA 87:1228, 1990).

Once a transformed plant cell or tissue has been obtained, it is possible to regenerate a full-grown plant from it. Means for regeneration vary from species to species. In one approach a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. Efficient regeneration will depend on the medium, on the genotype, and on the history of the culture. If these three variables are controlled, then regeneration is usually reproducible and repeatable. Plant regeneration is described, for example, in Evans, et al., Handbook of Plant Cell Cultures, Vol. 1: (MacMillan Publishing Co., New York, 1983); and Vasil I. R. (ed.), Cell Culture and Somatic Cell Genetics of Plants, Acad. Press, Orlando, Vol. I, 1984, and Vol. III, 1986). Practically all plants can be regenerated from cultured cells or tissues, including monocots, dicots, gymnosperms, etc.

After the DNA construct is stably incorporated in transgenic plants, it can be transferred to other plants by sexual crosses or by asexual propagation. With respect to sexual crossing, any of a number of standard breeding techniques can be used depending upon the species to be crossed. Cultivars can be propagated in accord with common agricultural procedures known to those in the field.

Identification of the *Zea mays* ZmproPEP3 Gene and ZmPEP3 Peptide

A novel gene, called ZmproPEP3, encodes a bioactive peptide, ZmPEP3, from *Zea mays*. The ZmproPEP3 gene was discovered through a sequence similarity search using the predicted protein sequence encoded by the previously published gene, ZmproPEP1 (GenBank Number: DY240150; Huffaker et al., Proc Natl Acad Sci USA. 103:10098, 2006). Query of GenBank *Z. mays* genomic sequence accessions with ZmproPEP1 was performed using the TBLASTN v 2.2.7 algorithm (Altschul, et al., Nucleic Acids Res 25: 3389, 1997). The query resulted in an alignment between the ZmproPEP1 sequence and a small region of the GenBank accession AC209428, a BAC clone containing a fragment of *Z. mays* chromosome 2. When translated, the BAC clone contained a predicted protein sequence similar to ZmproPEP1, encoded between position 145,897 and 146,424, that we designated ZmproPEP3. FIG. 1 shows the initial alignment of the protein sequence encoded by the ZmproPEP3 gene (Sbjct) with that of the ZmproPEP1 gene (Query). The fragment of the BAC clone containing the full-length predicted open reading frame aligned with the protein sequence encoded therein is exhibited in FIG. 2.

Several features of the ZmproPEP3 gene and encoded protein sequence are conserved characteristics shared by the two known families of plant bioactive peptide hormones known to regulate defense responses, the Systemins and the PEPs (McGurl et al., Science. 255:1570, 1992; Huffaker et al., Proc Natl Acad Sci USA. 103:10098, 2006). First, the gene encodes a small protein; ZmproPEP3 is predicted to be 146 amino acids long. All other known precursors encoding endogenous peptide regulators of defense responses are between 92 and 200 amino acids in length. Second, the precursor protein is highly enriched in glutamate/aspartate and lysine/arginine residues. Third, the bioactive peptide sequence, ZmPEP3, (shown in blue) is located at the carboxyl terminal of the protein and is preceded by several hydrophobic residues (orange) that may be important to peptide processing.

The ZmproPEP3 protein also contains several attributes specific to the proPEP precursor family of proteins, (see Table 1 for proPEP family). The latter half of the predicted bioactive peptide region is strongly characteristic of PEP family peptides. In particular, the glycine residue 7 positions away from the C-terminus (underlined; the 17$^{th}$ residue inward from the active peptide amino terminus) is required for activity in the *Arabidopsis* peptides and absolutely conserved across all family members (Pearce et al., Peptides. 12: 2083, 2008). Also, the final carboxyl-terminal asparagine residue (also underlined) is very highly conserved, and the enriched glycine, histidine and serine residue content in this region is indicative of a PEP family peptide.

TABLE 1 identified proPEPs

| | |
|---|---|
| American Sweet Flag *Acorus americanus* | Genbank #DT577959 |
| Bamboo1 *Bambusa edulis* | Genbank #FG551940 |
| Barley2 *Hordeum vulgare* | GenBank #DN189844 |
| *Barnadesia spinosa* | GenBank #GE526671 |
| *Brachypodium distachyon* | Genbank #EI141006 |
| Canola2 *Brassica napus* | GenBank #AY382680 |
| Canola3 *Brassica napus* | GenBank #ES912173 |
| Canola4 *Brassica napus* | GenBank #ES952301 |
| Canola5 *Brassica napus* | GenBank #EE406813 |
| Canola6 *Brassica napus* | GenBank #DV643333 |
| Cassava *Manihot esculenta* | Genbank #DV443747 |
| Chicory *Cichorium intybus* | Genbank #FL673090 |
| Clementine *Citrus clementina* | GenBank #ET086727 |
| Cotton alternative *Gossypium hirsutum* | GenBank #ES806527 |
| Dandelion *Taraxacum officinale* | Genbank #DY837292 |
| Eggplant *Solanum melongena* | Genbank #FS022013 |
| Endive *Cichorium endivia* | Genbank #EL364243 |
| Gerbera *Gerbera* hybrid | Genbank #AJ756162 |
| Grape1 *Vitis vinifera* | Genbank #CF604664 |
| Grapefruit *Citrus paradise* | Genbank #EB687264 |
| Lettuce *Lactuca sativa* | PlantGDB ID# PUT-157a-Lactuca_sativa-4606 |
| Lotus-*japonicus*1 | GenBank #AP010622 |
| Lotus-*japonicus*2 | Genbank #AP010194 |
| Madagascar-periwinkle *Catharanthus roseus* | Genbank #FD419202 |
| Maize3 *Zea mays* | Gene Locus ID #GRMZM2G339117 |

TABLE 1-continued identified proPEPs

| | |
|---|---|
| Maize5 *Zea mays* | Gene Locus ID #GRMZM2G141071 |
| Maize6 *Zea mays* | Gene Locus ID #GRMZM2G440972 |
| Maize7 *Zea mays* | Gene Locus ID #GRMZM2G325683 |
| *Medicago truncatula* 2 | Genbank #CU633466 |
| Oak-tree *Quercus robur* | GenBank #FP065216 |
| Oil-Palm1 *Elaeis guineensis* | Genbank #EL686712 |
| Orange *Citrus sinensis* | Genbank #DC900450 |
| Peanut *Arachis hypogaea* | Genbank #EE126324 |
| Peanut-Diploid *Arachis ipaensis* | Genbank #GW970655 |
| Pepper *Capsicum annum* | Genbank #CA519466 |
| Perennial-lettuce *Lactuca perrenis* | Genbank #DW102112 |
| Petunia *Petunia axillaris* | Genbank #FN004638 |
| Poplar2 *Populus trichocarpa* | Genbank #XM_002327286 |
| Prickly-Lettuce1 *Lactuca serriola* | Genbank #DW122287 |
| Radish1 *Raphanus sativus* | Genbank #EX896848 |
| Radish2 *Raphanus sativus* | Genbank #EW729774 |
| Safflower *Carthamus tinctorius* | Genbank #EL402550 |
| Snapdragon *Antirrhinum majus* | GenBank #AJ792052 |
| Sorghum1 *Sorghum* bicolor | Genbank #CW229591 |
| Sorghum2 *Sorghum* bicolor | Genbank #EI692236 |
| Sorghum3 *Sorghum* bicolor | Genbank #CW315024 |
| Soybean4 *Glycine max* | Genbank #BW669245 |
| Spotted-Knapweed *Centaurea maculosa* | Genbank #EH750095 |
| Swamp She-oak *Casuarina glauca* | Genbank #CO037501 |
| Switchgrass *Panicum virgatum* | Genbank #DN148560 |
| Tobacco *Nicotiana benthamiana* | Genbank #EH365820 |
| Turnip1 *Brassica rapa* | GenBank #EX120162 |
| Turnip2 *Brassica rapa* | GenBank #AC166741 |
| Turnip3 *Brassica rapa* | GenBank #AC189289 |
| Wheat3 *Triticum aestivum* | Genbank #BQ765489 |
| Wild-Lettuce *Lactuca virusa* | Genbank #DW151494 |
| Wild-Radish1 *Raphanus raphanistrum* | Genbank #EX776811 |
| Wild-Radish2 *Raphanus raphanistrum* | Genbank #EY896858 |
| Willowleaf-Lettuce *Lactuca saligna* | Genbank #DW048726 |

The gene structure of the ZmproPEP3 gene encoding the precursor protein is also characteristic of proPEP family genes. The gene is predicted by splice site prediction programs (Brendel et al., DNA. Nucl. Acids Res. 26: 4748, 1998) to contain a single small intron (shown in grey), the size and position of which is common to almost all proPEP family genes. Additionally, the ZmproPEP3 gene is located on *Z. mays* chromosome 2 very near the ZmproPEP1 gene, which is located from position 93,632 to 94,170 on the same BAC clone, AC209428. In *Arabidopsis*, the proPEP gene family consists of eight members, four of which are tandemly arrayed at one locus on chromosome 5, while three others are tandemly arrayed at another locus (Huffaker et al., Proc Natl Acad Sci USA. 103:10098, 2006). Many of the proPEP genes in canola and rice are also tandemly arrayed along their respective chromosomal loci (A. Huffaker, unpublished data).

While the ZmproPep3 gene and encoded precursor protein and predicted bioactive peptide contained therein display many features of the proPEP gene/protein family, the peptide deviates in several significant ways from the previously identified PEP peptides. The multiple proline residues found in the amino half of the ZmPEP3 peptide are not characteristic of PEP peptides, but are a defining feature of systemin peptides, making ZmPEP3 a structural hybrid of the two families.

Despite these similarities to both families, the ZmPEP3 peptide is unique among the endogenous plant defense peptides for its comparatively very low isoelectric point (pI). The presence of numerous basic amino acids and a high pI (9 or higher) is diagnostic of both systemin and PEP peptides, giving them a net positive charge at physiological pH conditions. For example, the ZmPEP1 peptide, the precursor of which was used to identify the ZmPEP3 precursor, has five arginine residues and a predicted pI of 12.18. However, the ZmPEP3 peptide contains a single arginine residue and has a predicted pI of only 5.37. Also unique to the ZmPEP3 peptide is a tryptophan residue at position 6; aromatic amino acids are uncommon in endogenous plant defensive signaling peptides, with just a small number of systemin family peptides containing a tyrosine residue (Pearce and Ryan, J Biol Chem. 278: 30044, 2003). No other known plant defense peptide encodes a tryptophan. Finally, the ZmPEP3 peptide contains an asparagine rather than a histidine at the carboxyl terminus; all other Plant Elicitor Peptides from maize terminate in a histidine. Together these residue peculiarities distinguish ZmPEP3 from other known peptide signals.

The ZmproPEP3 gene was cloned and sequenced from both the Golden Queen and B73 varieties of *Z. mays*. Both sequences were nearly identical to the original sequence contained in the BAC clone fragment of GenBank Accession AC209428. An alignment of the predicted protein encoded by both cloned genes with the protein encoded by AC209428 is shown in FIG. 1. As in the database accession, the B73 sequence we obtained encoded a predicted protein of 146 base pairs with two substitutions within the precursor region, a serine for a proline and a histidine for an arginine (marked in green). The gene from Golden Queen encoded one less alanine in the stretch of alanines encoded in the precursor, with 6 instead of 7, making the predicted protein 145 amino acids in length. The protein encoded by the Golden Queen gene deviated from the predicted protein encoded by the database accession at four positions (in orange). The cloned Golden Queen gene shared 96% identity with the cloned B73 gene. The predicted bioactive peptide (in blue) contained in the encoded precursor was identical for both cloned genes and the database accession. The full length genomic sequence, predicted mRNA and protein sequences for both B73 and Golden Queen ZmproPEP3 genes are contained in FIG. 3.

The ZmPeP3 peptide can be expressed in plants or plant cells under the control of an operably linked promoter that is capable of expression in the plant or plant cell, including but not limited to, constitutive, tissue-specific or inducible promoters. Any well-known method can be employed for plant cell transformation, culture, and regeneration in the practice of the present invention with regard to a particular plant species. Conventional methods for introduction of foreign DNA into plant cells include, but are not limited to: (1) *Agrobacterium*-mediated transformation (Lichtenstein and Fuller In: Genetic Engineering, Vol 6, Rigby, ed., London, Academic Press, 1987; and Lichtenstein and Draper, in: DNA Cloning, Vol II, Glover, ed., Oxford, IRI Press, 1985); (2) particle delivery (see, e.g., Gordon-Kamm et al., Plant Cell 2:603, 1990; or BioRad Technical Bulletin 1687), (3) microinjection (see, e.g., Green et al., Plant Tissue and Cell Culture, Academic Press, New York, 1987), (4) polyethylene glycol (PEG) procedures (see, e.g., Draper et al., Plant Cell Physiol. 23:451, 1982); Zhang and Wu, Theor. Appl. Genet. 76:835, 1988), (5) liposome-mediated DNA uptake (see, e.g., Freeman et al., Plant Cell Physiol. 25:1353, 1984), (6) electroporation (see, e.g., Fromm et al., Nature 319:791, 1986); and (7) vortexing method (see, e.g., Kindle, Proc. Natl. Acad. Sci. USA 87:1228, 1990).

Once a transformed plant cell or tissue has been obtained, it is possible to regenerate a full-grown plant from it. Means for regeneration vary from species to species. In one approach a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. Efficient regeneration will depend on the medium, on the genotype, and on the history of the culture. If these three variables are controlled, then regeneration is usually reproducible and repeatable. Plant regeneration is described, for example, in Evans, et al., Handbook of Plant Cell Cultures, Vol. 1: (MacMillan Publishing Co., New York, 1983); and Vasil I. R. (ed.), Cell Culture and Somatic Cell Genetics of Plants, Acad. Press, Orlando, Vol. I, 1984, and Vol. III, 1986). Practically all plants can be regenerated from cultured cells or tissues, including monocots, dicots, gymnosperms, etc.

After the DNA construct is stably incorporated in transgenic plants, it can be transferred to other plants by sexual crosses or by asexual propagation. With respect to sexual crossing, any of a number of standard breeding techniques can be used depending upon the species to be crossed. Cultivars can be propagated in accord with common agricultural procedures known to those in the field.

Compositions comprising the ZmPEP3 peptide or polypeptide compositions may further comprise biologically acceptable carriers and/or other substances used in formulating peptides and polypeptides. Additional simple modifications to facilitate transport of polypeptides such as ZmPep3 and even larger proteins across hydrophobic barriers and into cells can likewise be utilized, including but not limited to, truncated forms of the peptide. Such compositions may be agricultural formulations that are suitable for application to plants. Accordingly, in another embodiment of the invention, plants or seeds of plants are provided that comprise such a composition applied to a plant or seed surface, respectively. Alternatively, solutions applied to the roots systems of soil grown plants via aqueous drenching have proven effective in related systems (Yamaguchi et al, Plant Cell 2010). When applied to plants under suitable conditions, such compositions induce the plants' innate immunity and enhancing their defense against attack by=herbivores and pathogens.

According to another embodiment of the invention, cells are provided that comprise ZmPEP3, including, but not limited to, plant, bacterial, fungal (including yeast), and insect cells. According to another embodiment, plants that comprise such cells are provided, including, but not limited to, plants of the family Poaceae, such as maize, wheat, sorghum, millets, rice, rye, oats, bamboo, Sugarcane, annual bluegrass, annual meadowgrass, *Poa annua*, orchardgrass, *Festuca* spp., sudangrass, ryegrass, Indiangrass, Bermudagrass, Bent grass, reeds and switchgrass. The invention further encompasses parts of such plants, including, but not limited to, seeds, seed pods, flowers, fruit, tubers, stems, cuttings, and pollen. The invention also encompasses products resulting from processing of such plants or parts thereof.

According to another embodiment of the invention, existing methods are cited for making a plant that comprises a transgene comprising a sequence that encodes the ZmPEP3 peptide operably linked to a plant promoter, such methods comprising sexually crossing a plant that comprises the transgene with a plant that lacks the transgene, thereby producing a plurality of progeny plants, and selecting a progeny plant comprising the transgene.

According to another embodiment of the invention, methods are provided for making a plant that comprises a transgene comprising a sequence that encodes the ZmPEP3 peptide operably linked to a plant promoter, the method comprising asexually reproducing a plant that comprises the transgene, thereby producing a plurality of progeny plants, and selecting a progeny plant comprising the transgene.

Agronomically and commercially important products and/or compositions of matter derived from transgenic plants according to the invention include, but are not limited to, animal feed, commodities, products and by-products that are intended for use as food for human consumption or for use in compositions and commodities that are intended for human consumption, including but not limited to plant parts, including but not limited to seeds, seed pods, flowers (including flower buds), fruit, tubers, stems, cuttings, pollen, and products derived from processing such plant parts, including but not limited to flour, meal, syrup, oil, starch, cakes, cereals, and the like. Such compositions may be defined as containing detectable amounts of a polynucleotide sequence of the invention as set forth herein, and thus are also diagnostic for any transgenic event containing such nucleotide sequences. These products are more likely to be derived from crops propagated with fewer pesticides and organophosphates as a result of their incorporation of the nucleotides of the present invention for controlling plant disease. For example, such commodities and commodity products can be produced from seed produced from a transgenic plant, wherein the transgenic plant comprises cells that express a defense signal protein of the present invention.

ZmPEP3 Regulates Expression of Both Herbivore and Pathogen Defense Genes

An embodiment of the invention is ZmPEP3 regulated expression of both herbivore and pathogen defense genes as well as herbivory-defense regulating signals by the ZmPEP3 and homologs thereof.

Plants respond to herbivore attack with sophisticated and dynamic immune responses that result in a suite of induced defenses. These responses include structural fortifications such as thorns, trichomes and cell-wall strengthening, as well as biochemical defenses. For example, antinutritive proteinase inhibitors (PINs) are systemically induced upon insect attack, but many other proteins contribute to anti-herbivory responses as well (Green and Ryan, Science 175:776, 1972). A number of enzymes limit protein availability in the midgut, whereas others destabilize insect peritrophic membranes (Chen et al., Plant Physiol 143:1954, 2007; Gooday, EXS 87:157, 1999; Vandenborre, Phytochemistry 72:1538, 2011). Plants also draw upon a complex arsenal of small molecule chemical defenses including terpenoids, alkaloids, phenylpropanoids, glucosinolates, benzoxazinoids and non-protein amino acids (Howe and Jander, Annu Rev Plant Biol. 59:41, 2008; Adio et al., Plant Cell 23:3303, 2011). These metabolites can act as feeding deterrents or negatively impact growth and fitness via direct toxicity or mimicry of insect hormones (Howe and Jander, Annu Rev Plant Biol. 59:41, 2008; Schmelz et al., Arch Insect Biochem Physiol. 51:204, 2002).

Herbivory also stimulates emission of a complex blend of volatiles that function as indirect defenses through oviposition deterrence and attraction of natural enemies such as parasitoids and predators (De Moraes et al., Nature. 410:577, 2001; Turlings et al., Science. 250:1251, 1990; Kessler and Baldwin, Annu Rev Plant Biol. 53:299, 2002; Rasmann, et al. Nature 434:732, 2005; Unsicker et al., Curr Opin Plant Biol. 12:479, 2009). These volatiles are also implicated in plant priming effects, alerting closely neighboring plants or tissues to potential attack and enabling a stronger and swifter response (Heil and Bueno, Proc Natl Acad Sci USA 104: 5467; 2007). As herbivory-induced volatile production is conserved across diverse plant species and perceived across trophic levels, these volatiles exert wide-ranging effects on ecological communities (Kessler and Halitschke, Curr Opin Plant Biol. 10:409, 2007; Poelman et al., Trends Plant Sci. 1310:534, 2008).

Previous studies with peptide regulators of plant defense revealed that by supplying an excised leaf with a solution of bioactive peptide, induced expression of defense genes regulated by that peptide may be observed. In tomato leaves supplied with the systemin peptide through their cut petiole, transcripts encoding anti-herbivore defense proteins and proteins involved in transduction of defense signaling increased in abundance as compared to controls supplied with water (Ryan, Biochim Biophys Acta 1477:112, 2000; Orozco-Cárdenas et al., Plant Cell 13: 179, 2001). Similarly, *Arabidopsis* leaves supplied with the AtPEP peptides through their cut petiole showed increased abundance in transcripts encoding pathogen-defense signaling proteins and antimicrobial proteins as compared to water-supplied leaves (Huffaker and Ryan, Proc Natl Acad Sci USA. 104:10732, 2007; Yamaguchi et al., Plant Cell 22:508, 2010). Therefore, an excised leaf assay was designed to probe whether the ZmPEP3 peptide might be an active signal in maize.

Suitable maize candidate genes for use as markers indicative of induced defense responses were selected through literature searches. Several pathogen defense markers were identified based on a microarray experiment that catalogued genes rapidly induced in maize kernels responding to inoculation with *Ustilago maydis* (Doehlemann et al., Plant J. 56:181, 2008). Other genes were chosen for their demonstrated role in conveying resistance to a pathogen (Chen et al., Phytopathology 94:938, 2004; Chen et al., Phytopathology 97:1094, 2007). Candidate genes of interest related to induced herbivore defenses were identified from a study compiling such marker genes (Erb et al., Plant J 59: 292, 2009). Finally, several genes that encode proteins responsible for the synthesis of defense related metabolites were identified for use as markers of induced defense (Frey et al., Proc Natl Acad Sci USA. 97:14801, 2000; Schnee et al., Plant Physiol 130: 2049, 2002; Köllner et al., Plant Cell 20: 482, 2008). Table 2 lists the GenBank accession numbers, citations and primer sequences pertinent to each marker gene chosen.

TABLE 2

| Gene Name | GenBank# | Cycles | Size (bp) | Source | Year |
| --- | --- | --- | --- | --- | --- |
| Actin | J01238 | 33 | 303 | Erb et al. | 2009 |
| ACC Oxidase | AY359573 | 27 | 281 | Doehlemann et al. | 2008 |
| Allene oxide synthase | AY488135 | 27 | 257 | Erb et al. | 2009 |
| Allene oxide cyclase | AY488136 | 27 | 295 | Erb et al. | 2009 |
| Endochitinase A | EU963425 | 33 | 311 | Doehlemann et al. | 2008 |
| EndochitinasePR-4 | EU968115 | 27 | 263 | Doehlemann et al. | 2008 |
| Endochitinase C | EU960726 | 27 | 345 | Doehlemann et al. | 2008 |
| Glutathione-S-Transferase 24 | AF244689 | 27 | 289 | Doehlemann et al. | 2008 |
| Glutathione-S-Transferase 36 | AF 244701 | 25 | 270 | Doehlemann et al. | 2008 |
| Glutathione-S-Transferase 30 | AF244695 | 30 | 312 | Doehlemann et al. | 2008 |
| Glutathione-S-Transferase 25 | AF 244690 | 37 | 348 | Doehlemann et al. | 2008 |
| Olutathione-S-Transferase 20 | AF244685 | 27 | 306 | Doehlemann et al. | 2008 |
| Glutathione-S-Transferase IV | U12679 | 27 | 252 | Doehlemann et al. | 2008 |

TABLE 2-continued

| Gene Name | GenBank# | Cycles | Size (bp) | Source | Year |
|---|---|---|---|---|---|
| Hevein | X82184 | 34 | 275 | Doehlemann et al. | 2008 |
| IGL3 Volatile Indole Synthase | AF 271383 | 33 | 308 | Frey et al.. | 2000 |
| LOX | AF465643 | 30 | 256 | Erb et al.. | 2009 |
| MAP Kinase 4 | A801 6801 | 27 | 348 | Doehlemann et al. | 2008 |
| OPR1 | AY921638 | 30 | 291 | Doehlemann et al. | 2008 |
| Osmotin | BT041029 | 34 | 286 | Doehlemann et al. | 2008 |
| PR Protein Precursor | BT039519 | 34 | 255 | Doehlemann et al. | 2008 |
| PM-bound Peroxidase 3-1 | EF059718 | 26 | 295 | Doehlemann et al. | 2008 |
| Peroxidase | AY1 07804 | 27 | 345 | Doehlemann et al. | 2008 |
| Cationic Peroxidase (A) | BT036551 | 34 | 276 | Doehlemann et al. | 2008 |
| Cationic Peroxidase (B) | AY107230 | 27 | 306 | Doehlemann et al. | 2008 |
| Polyphenol Oxidase PP02 | AY1 03683 | 26 | 298 | Doehlemann et al. | 2008 |
| PR1 | BT034431 | 33 | 271 | Doehlemann et al. | 2008 |
| Thaumatin | BT041158 | 37 | 295 | Doehlemann et al. | 2008 |
| Glyoxylase I | AY241545 | 27 | 337 | Chen et al. | 2004 |
| Periredoxin-Antioxidant | DQ378060 | 30 | 336 | Chen et al. | 2007 |
| BETL3 Defensin | AJ133530 | 37 | 330 | Erb et al. | 2009 |
| Esr-6 Defensin | AJ849917 | 37 | 250 | Erb et al.. | 2009 |
| Terpene Synthase 1 (TPS1) | AF529266 | 25 | 277 | Schnee et al. | 2002 |
| Terpene Synthase 11 (TPS11) | NM_001112480 | 37 | 285 | Doehlemann et al. | 2008 |
| Terpene Synthase 23 (TPS23) | EU259634 | 25 | 312 | Kollner et al. | 2008 |

FIG. 4 demonstrates changes in expression of several defense-related genes in response to treatment with ZmPEP3 peptide for various lengths of time. Over a 16.5 hour timecourse, excised maize leaves were supplied with either a solution of ZmPEP3 peptide or with a water control. Based on the average volume of ZmPEP3 solution taken up by the maize leaves, each leaf was exposed to around 1.8 nMols of peptide per gram of leaf material over the time course study. Zero hour treatments indicate leaves that were immediately harvested at the beginning of the study; the other time points refer to hours elapsed after leaves were excised and placed into solution. As a control to observe herbivory-induced expression of these genes, a timecourse of exposure to herbivory by Spodoptera frugiperda (fall armyworm, FAW) was performed for comparison. As described in the Material and Methods, when using the semi-quantitative RT-PCR analysis technique, observed band intensity is indicative of initial transcript abundance in a sample, thus bands of greater intensity represent sample with enriched transcript abundance.

The ZmActin1 gene shown in the top row of both the upper and lower panel of FIG. 4 has been experimentally proven to be a reliable control gene for studies of changes in transcript abundance because the expression is steady under a variety of conditions in all tissues of the plant (Erb et al., Plant J 59: 292, 2009). The gene was employed in these studies to ensure that changes in transcript abundance observed for other genes were not because of variation in the amount of RNA from sample to sample. The top panel of FIG. 4 is composed of photographs of gel electrophoretic visualization of amplified transcripts from each leaf RNA sample, whereas the bottom panel represents those from midvein RNA. Expression of ZmActin1 was steady across all observed samples, but expression of the representative defense genes shown in the rows below was induced by ZmPEP3 treatment.

The endochitinase A gene encodes a class of antifungal protein that degrades fungal cell walls and is rapidly induced in maize kernels responding to pathogen infection (Doehlemann et al., Plant J. 56:181, 2008). ZmPEP3 and herbivory induce increased transcript levels at all early time points. At the later time points the transcript transiently increases in abundance in the excised water-supplied leaves as well, indicating wound-inducible gene expression. However the amplified transcript from these samples never reaches the magnitude of band intensity found from the herbivory or peptide-supplied excised leaves, and dissipates by the final time point.

Allene oxide synthase (AOS) is a protein required for the biosynthesis of an important class of plant oxylipin hormones that regulate defense responses to both herbivores and pathogens, the jasmonates. As shown in row 3 of each panel in FIG. 4, the AOS transcript increase in abundance as early as 2 hours in response to ZmPEP3 and herbivory, and at later time points AOS transcript levels are markedly increased in both treatments, whereas expression levels in water-supplied leaves have decline.

The terpene synthase 23 gene (TPS23) synthesizes a sesquiterpene, 0-caryophyllene, that has been shown to contribute to herbivore defense in maize plants via recruitment of both parasitic wasps and entomopathogenic nematodes that prey upon insect herbivore pests (Köliner et al., Plant Cell 20: 482, 2008). Similarly to AOS, the expression of TPS23 is transiently wound-inducible at the early time points, but at later time points transcript abundance has increased greatly in leaves exposed to ZmPEP3 or herbivory, but has receded in the water-supplied leaves.

The peroxidase gene shown in the $5^{th}$ row of both panels in FIG. 4 is rapidly inducible in kernels of maize plants upon infection with a fungal pathogen (Doehlemann et al., Plant J. 56:181, 2008). Pathogen inducible peroxidases such as the one encoded by this gene are classified as Class 9 Pathogenesis-Related proteins (PR-9). They are believed to contribute to plant pathogen defense by two mechanisms, strengthening the plant cell wall by promoting crosslinking reactions between cell wall component molecules, and ameliorating pathogen-induced oxidative damage through detoxification reactions (Van Loon and Van Strien, Physiol. Mol. Plant Pathol. 55:85, 1999). Whereas peroxidase transcript was not detectable in leaves supplied with water, ZmPEP3-supplied leaves showed marked induction of transcript accumulation at later timepoints.

The final row of both panels in FIG. 4 shows expression analysis of the IGL gene, which encodes a biosynthetic enzyme required for synthesis of the volatile indole that is detected in herbivore-damaged leaves (Frey et al., Proc Natl Acad Sci USA. 97:14801, 2000). This indole is a component of the complex chemical blend released by maize plants to attract parasitoid wasps that prey upon insect herbivores. IGL is wound-responsive early in the timecourse, but strongly induced only in the leaves supplied with ZmPEP3 or exposed to herbivory at the later time points.

Figure 7:
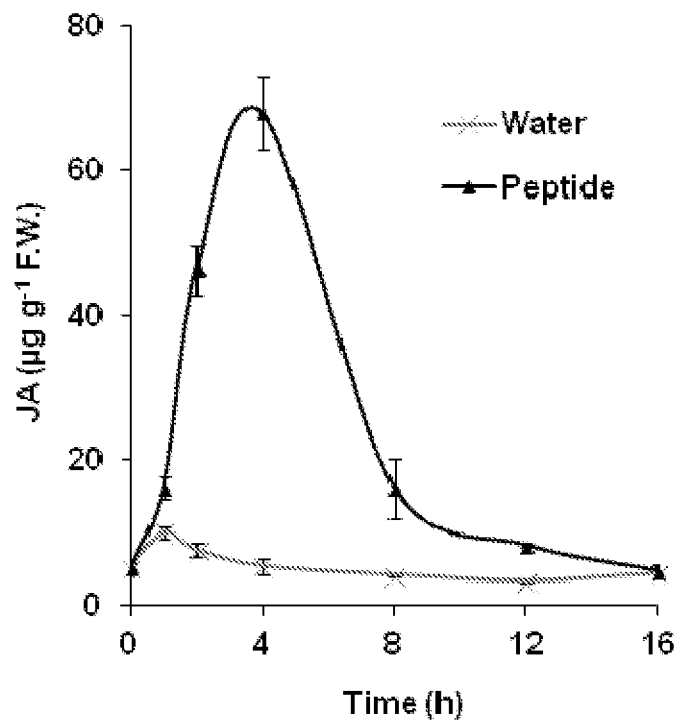
FIG. 7 is a timecourse graph of jasmonic acid production in leaves in response to treatment with 1.8 nM ZmPEP3. Jasmonic acid is a plant hormone associated with elicitation of herbivore defense responses.
Figure 8:
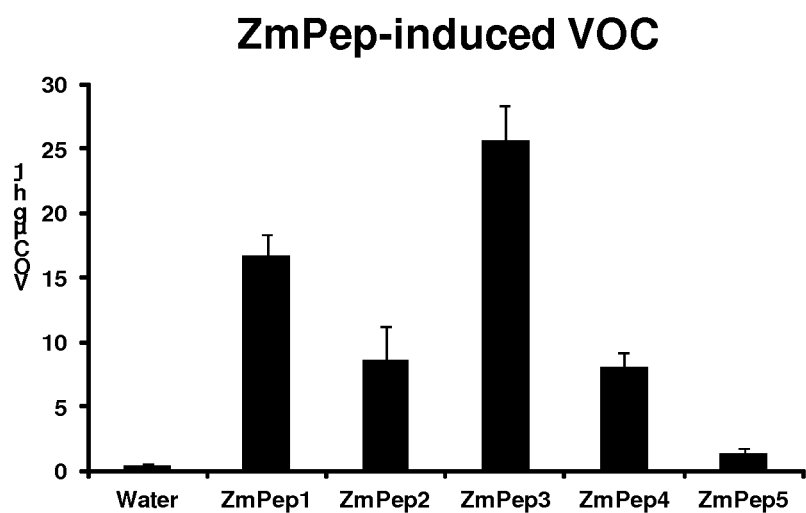
FIG. 8 is a graph of an alignment of five ZmPep peptides from maize, followed by quantification of total emitted volatile metabolites collected from excised leaves after a 16 hour treatment with water or with solutions of ZmPEP peptides.

The gene transcripts shown in FIG. 4 are a subset of the defense-related genes found to be induced by ZmPEP3 peptide in the excised leaf assays. Including these, a total of twenty genes have been identified as ZmPEP3-responsive. All can be classified as pertaining to four broad categories of defense-related genes; those encoding proteins that are directly antimicrobial, those encoding proteins that synthesize secondary metabolites associated with defense, those encoding proteins that are involved in reactive oxygen species-based signal transduction and detoxification, and those that encode biosynthetic proteins for the two main plant small molecule hormone regulators of defense, ethylene and oxylipins. To obtain a more global perspective of gene expression regulated by ZmPEP3, a microarray experiment was performed to compare expression levels in ZmPEP3 vs. water-treated leaves after 8 hours. FIG. 6 lists the genes upregulated 10-fold or more in peptide-treated leaves; many of these genes are anti-herbivore defense genes or genes encoding biosynthetic enzymes for the plant defense hormone jasmonic acid. In FIG. 7, real-time quantification of expression levels of genes associated with direct and indirect herbivore defenses confirms that ZmPEP3 is a strong regulator of both defense responses. Genes encoding terpene synthases were upregulated more than a thousand-fold in peptide-treated leaves, as were genes encoding proteinase inhibitor proteins which are directly defensive. FIG. 8 lists defense-associated genes discovered to be induced by the ZmPEP3.

ZmPEP3 Regulates Production of Defense-Related Metabolites

Figure 9:
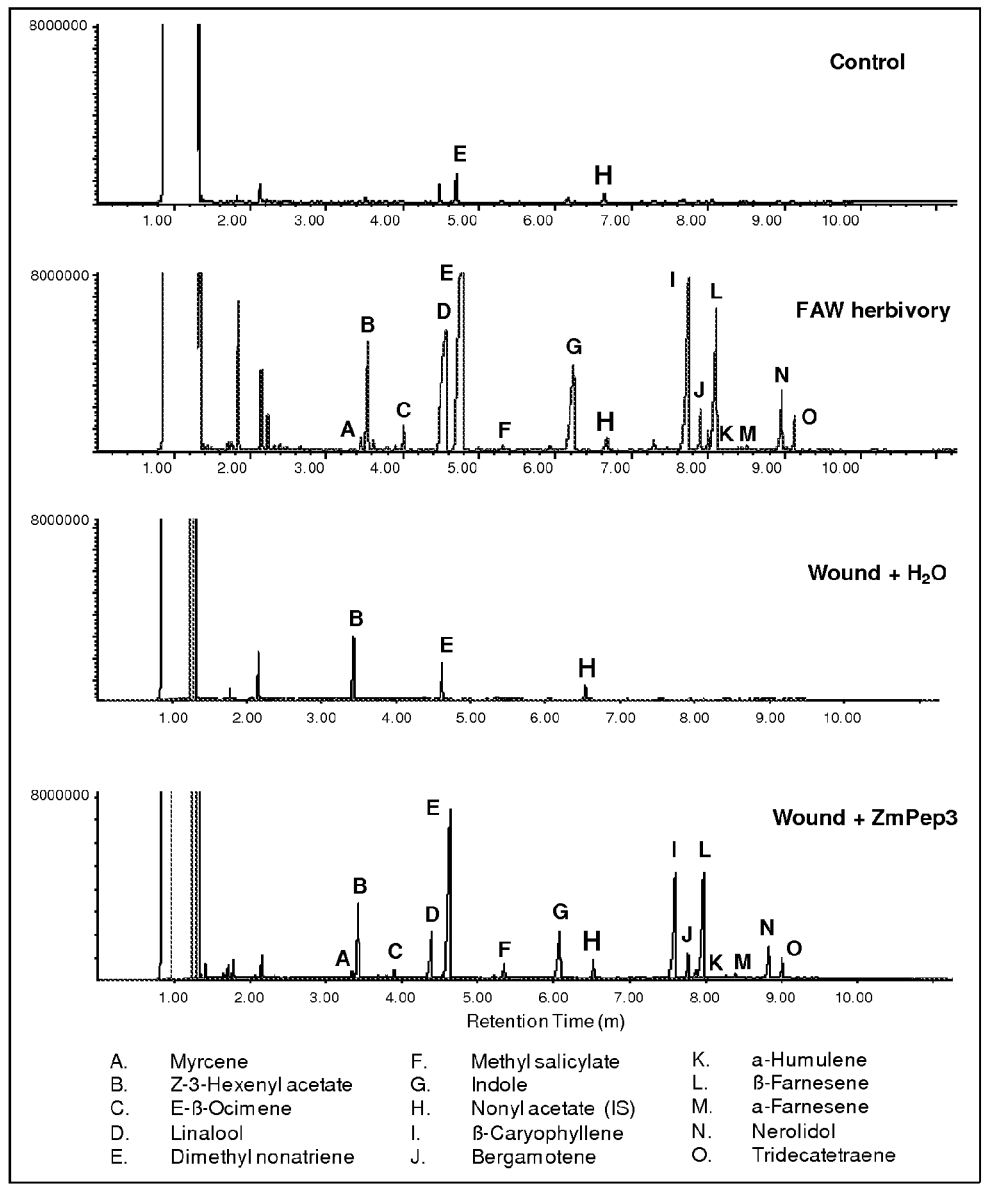
FIG. 9 is a gas chromatograph analysis of volatiles emitted from untreated maize leaves, maize leaves subjected to herbivory by S. frugiperda, maize leaves treated with water, and maize leaves treated with ZmPEP3 peptide. Herbivory and ZmPEP3 peptide induce production of the same spectrum of volatile metabolites, as quantified using a nonyl acetate internal standard.

A further embodiment is ZmPEP3 regulated production of defense-related metabolites. The elicitor-induced phytohormones JA and ethylene (ET) function as signals integral to initiation of protective responses against pathogens and herbivores (Howe and Jander, Annu Rev Plant Biol. 59:41, 2008). N-Linolenoyl-L-glutamine (Gln-18:3) is an elicitor present in the oral secretions of many Lepidopteran species that exhibits strong activity in promoting both phytohormone production and emission of herbivory-associated volatiles (Schmelz et al., Proc Natl Acad Sci USA. 106:653, 2009; Pare et al., Proc Natl Acad Sci USA 95:13971, 1998). Just as ZmPEP3 induced expression of genes encoding biosynthetic enzymes for the defense hormone jasmonic acid, jasmonic acid was found to accumulate in ZmPEP3-treated leaves as shown in FIG. 9. In a comparative treatment of leaves with low equivalent quantities of either ZmPep3 or Gln-18:3, both resulted in elicitation of JA and ET synthesis. However, ZmPep3-induced increases were of greater magnitude and longer duration. This difference was also reflected at the transcript level; both ZmPep3 and Gln-18:3 treatments caused significantly increased accumulation of transcripts encoding biosynthetic enzymes for ET and JA, ACC Oxidase, Allene Oxide Synthase (AOS) and Allene Oxide Cyclase (AOC; FIG. 2C). Consistent with ET and JA production, greater quantities of transcript corresponding to ACC Oxidase and AOC were detected in ZmPep3-treated as compared to Gln-18:3-treated leaves.

As discussed above treatment of leaves with the ZmPEP3 peptide induced expression of several genes encoding biosynthetic proteins for a variety of defense-associated secondary metabolites. The IGL and terpene synthase genes (TPS) listed in FIG. 6 generate volatile terpenoids and indole that contribute to herbivore defense via recruitment of wasps that parasitize insect pests of the maize plant (Turlings et al., Science 250:1251, 1990; Frey et al., Proc Natl Acad Sci USA. 97:14801, 2000; Schnee et al., Plant Physiol 130: 2049, 2002; Köllner et al., Plant Cell 20: 482, 2008). Because ZmPEP3 induced expression of these genes, we analyzed the emitted volatile profile of leaves supplied with ZmPEP3 as compared to water-supplied leaves.

FIG. 11 presents a profile of volatile compounds emitted in thirty minutes by water-supplied leaves versus that of herbivory-subjected or ZmPEP3-supplied leaves as analyzed by gas chromatographic separation. Two molecules were detected in water-supplied leaf emissions, dimethyl nonatriene and tridecatetraene, both of which are strongly induced by wounding. Many molecules are detected in the leaves exposed to herbivory or to ZmPEP3 that are not present in the water-supplied leaves at this scale, including myrcene, E-β-ocimene, linalool, methyl salicylate, indole, β-caryophyllene, bergamotene, α-humulene, β-farnesene, α-farnesene, and nerolidol. Production of several of these molecules correlates with the gene expression data shown above; IGL catalyzes synthesis of indole, whereas TPS1 produces nerolidol and farnesene, TPS10 generates bergamotene and TPS23 is involved in β-caryophyllene synthesis.

All of these molecules are produced in response to herbivore or herbivore-associated elicitor molecules and act to recruit natural enemies of herbivores feeding on maize leaves (Turlings et al., Science 250:1251, 1990; Alborn et al., Science, 276:945, 1997; Kessler and Baldwin, Science, 291: 2141, 2001, Schmelz et al., Proc Natl Acad Sci USA 103: 8894, 2006). However, while many insect-generated elicitors are known to regulate production of these chemicals, no endogenous plant signal has been previously identified that induces production of the full spectrum of these molecules. ZmPEP3 is the first described plant-produced signal regulating this response.

Figure 10:
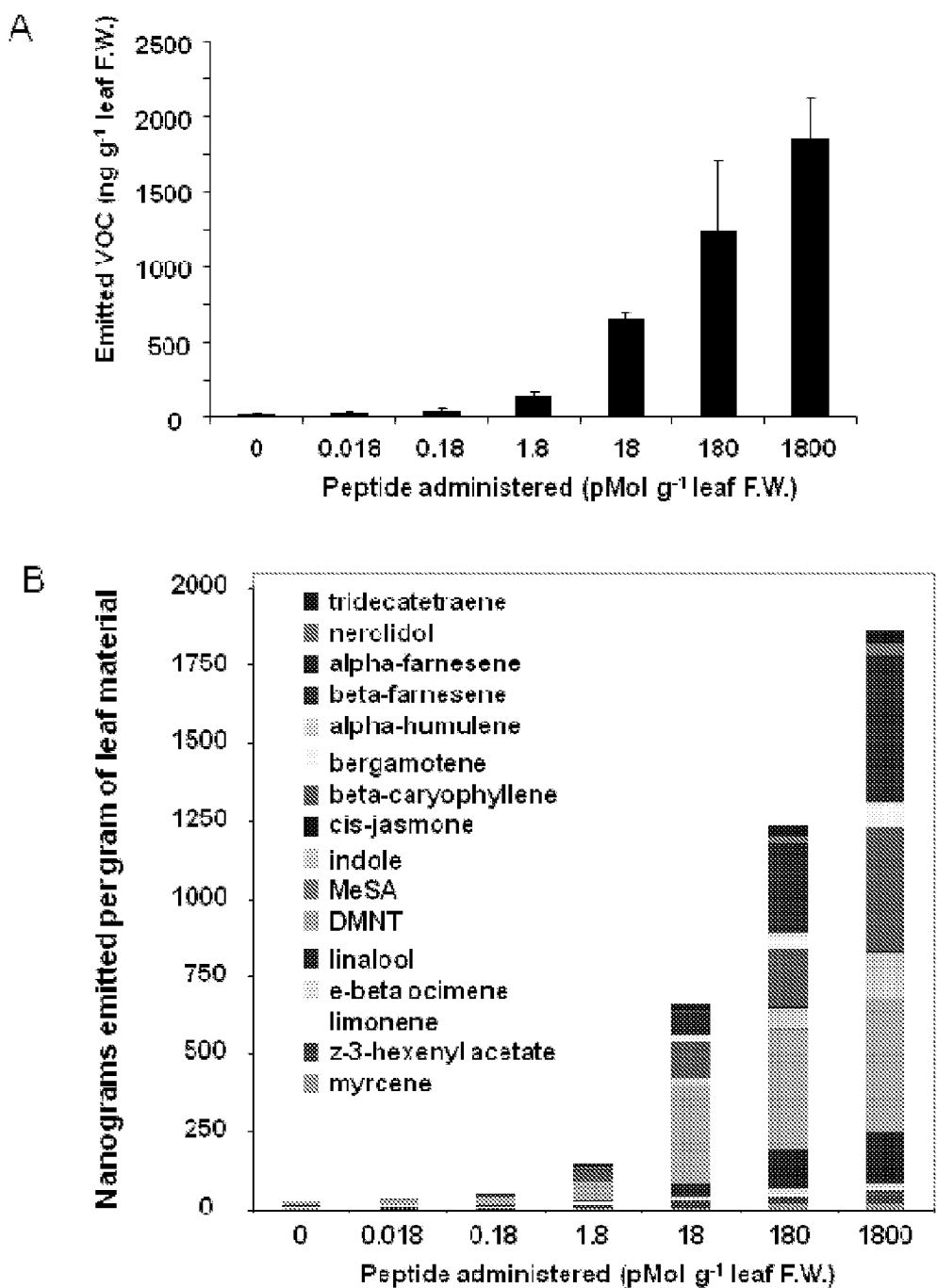
FIG. 10 is a graph of the dose-dependence of ZmPEP3-induced volatile metabolite; application of increasing amounts of peptide result in increased emission of volatiles. The top panel A shows total emitted volatiles, while the bottom panel B indicates the relative quantity of each individual chemical component.

Induced emission of these volatile compounds is regulated by the peptide in a dose-responsive way. FIG. 10 is a graph of the total nanograms of defense volatile compounds emitted per gram of leaf material in response to increasing concentrations of ZmPEP3 administered as collected over 30 minutes. While the volatile profile of leaves treated with 18 or 180 fMols of peptide per gram of leaf are almost the same as leaves supplied with water, significant increases in defense volatile emission are observable at concentrations as low as 1.8 pMol ZmPEP3 peptide per gram of leaf material. Each ten-fold increase in concentration of peptide administered yields a stronger induction of volatile emission with a 91% increase observed at the highest concentration applied, 1.8 nMol peptide per gram of leaf material, as compared to the water-supplied leaves.

FIG. 11 lists the nanograms of each volatile substance emitted per gram of leaf material over a six hour period from leaves supplied with either water or ZmPEP3 peptide. The wound-inducible chemicals dimethyl nonatriene (DMNT) and tridecatetraene are major component of both profiles, although peptide-supplied leaves emit 6 fold more DMNT. The increase in emission of other volatile defense metabolites from ZmPEP3-treated leaves over that of water-treated leaves is of a greater magnitude. For instance, alpha-bergamotene emission increased over a thousand fold, beta-farnesene over 900-fold, nerolidol emission increased 360-fold and the increased emissions of both beta-caryophyllene and indole were over 100-fold.

ZmPEP3-Induced Metabolites have Broad Antimicrobial Activity

A further embodiment is ZmPEP3-induced metabolites with broad antimicrobial activity.

As shown above, ZmPEP3 regulates expression of genes encoding antimicrobial defense proteins and also induces synthesis and emission of volatile compounds known to attract parasitoid wasps as an indirect herbivore defense strategy. We hypothesized that these herbivore-induced metabolites may serve an endogenous purpose to the plant in addition to their external role as chemoattractants. Although these chemicals are emitted from leaves as volatiles, they are also present within the leaf itself, and some have been observed to be spatially produced within a very close radius of the damage site on a leaf (E. Schmelz, unpublished data). Because the external barriers to pathogen invasion are compromised at damage sites, these wounds facilitate entrance of potentially pathogenic microorganisms. Thus prevention of microbial invasion and proliferation at these sites is an important contributing factor to plant disease resistance. We hypothesized that if the ZmPEP3-induced chemicals had antimicrobial properties, then through their concentration at herbivore-damaged sites they could contribute to pathogen defense at these locations in addition to recruiting natural enemies of the herbivore.

To test this hypothesis we designed an assay to examine the antimicrobial properties of each of the ZmPEP3-induced metabolites. Microbial growth medium was supplemented with the chemicals and then inoculated with a variety of pathogens. These organisms included several fungi that had been isolated off of germinating maize kernels, *Aspergillus niger*, *Trichoderma viride*, *Rhizopus* sp., *Penicillium* sp., *Aspergillus flavus* and *Fusarium graminearum*. To screen for breadth of antimicrobial activity of the ZmPEP3-induced metabolites, two phytopathological strains of bacteria were also inoculated into the chemical-supplemented medium; *Pseudomonas syringae* pv. tomato DC3000 (Pst) and virulent *Xanthomonas campestris* pv. *vesicatoria* (Xcv vir).

Figure 13:
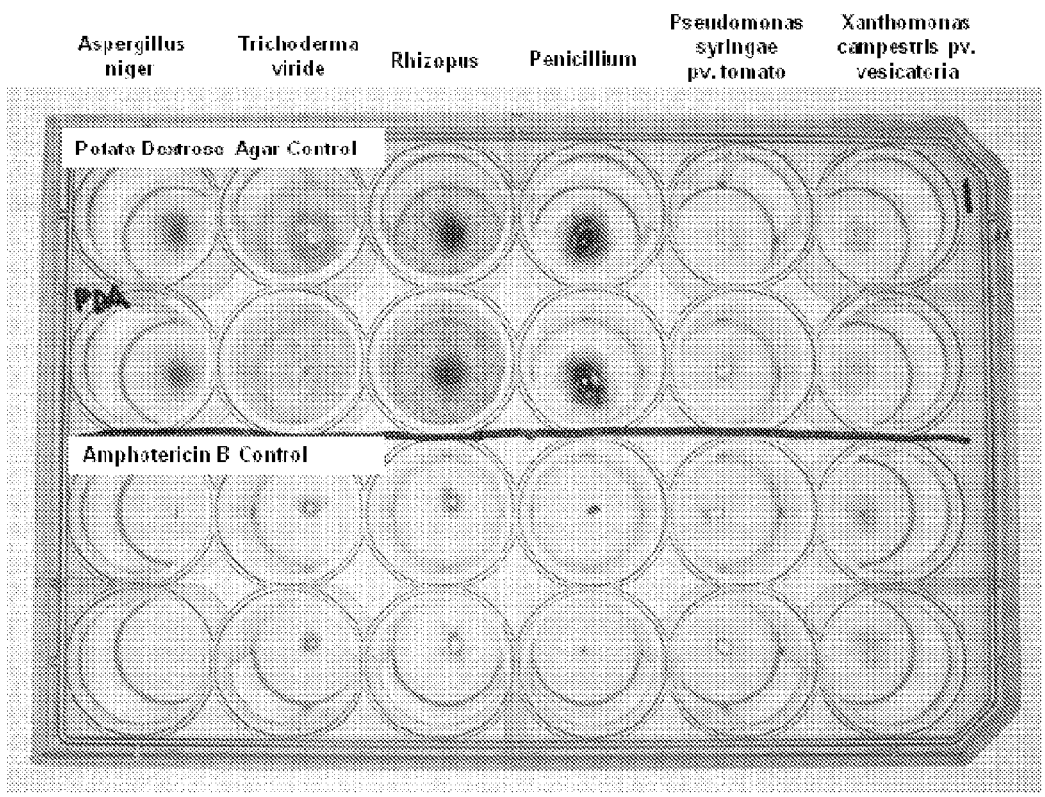
FIG. 13 is a photo of the assay for antimicrobial properties of ZmPEP3-induced chemicals. A plate containing control growth medium (top rows, Potato Dextrose Agar—PDA) and PDA supplemented with an antimycotic agent (bottom rows), amphotericin B, is shown three days after inoculation with six microorganisms. A. niger, T. viride, Rhizopus and Penicillium are fungi isolated from germinating maize kernels; P. syringae and X. campestris are phytopathological bacteria.

FIG. 13 illustrates one such experiment; shown in the top two rows is the growth characteristic of each pathogenic organism on unsupplemented control potato dextrose agar medium after three days. Each organism was inoculated into a center well, and has grown outwards from that well, and all of the fungi have initiated spore production. The bottom two rows in FIG. 13 demonstrate growth of each organism on a widely used antimycotic agent, amphotericin B. After three days on the antimycotic-supplemented medium, the fungi have not spread from the center well, whereas the bacteria (*P. syringae* and *X. campestris*) have proliferated unaffected by the antifungal agent.

Figure 14:
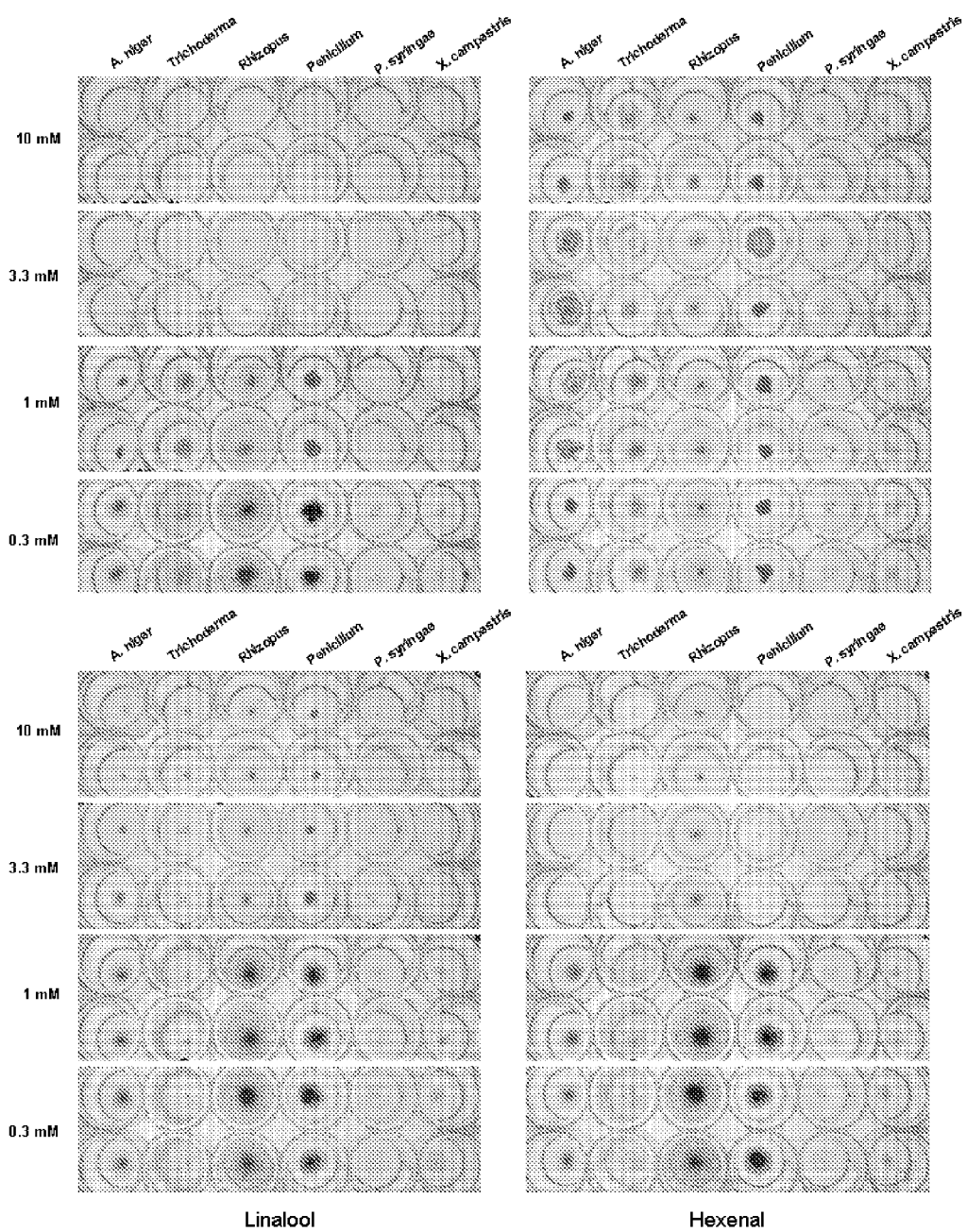
FIG. 14 is a photo of phytochemicals induced by ZmPEP3 as active antimicrobial agents. Four maize metabolites present in excised leaves supplied with ZmPEP3 peptide have antimicrobial properties; indole (top left), nerolidol (top right), linalool (bottom left) and hexenal (bottom right). Each metabolite was mixed into PDA and titrated downward in three-fold serial dilutions such that concentrations in the growth medium ranged between 10 mM and 0.3 mM. Assays are shown three days after inoculation.

In FIG. 14 assays of the ZmPEP3-induced volatiles with the strongest effects on growth and morphology are shown. At concentrations of 10 and 3.3 mM, indole, linalool and hexenal prevented growth of both the fungal and bacterial pathogens. Indole still had a moderate limiting effect on fungal growth at a 1 mM concentration, whereas the effects on microbial growth of linalool and hexenal were reduced at this concentration. Indole was particularly effective at limiting bacterial growth even at the lowest concentration tested. Nerolidol did not limit microbial growth at any concentration but was instead a strong inhibitor of sporulation for all fungi, at all concentrations tested.

Figure 15:
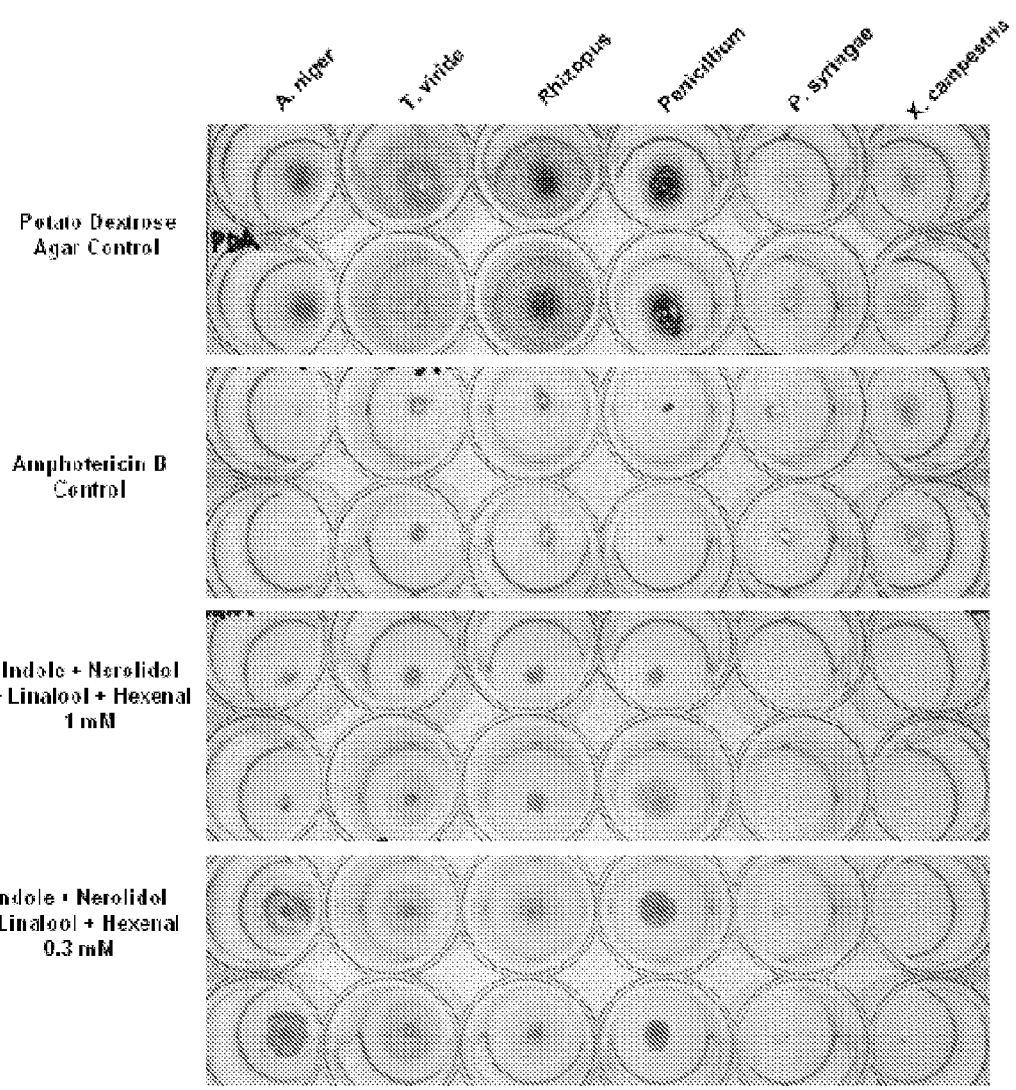
FIG. 15 is a photo of defense metabolites induced by the ZmPEP3 peptide have potentiating antimicrobial activity when used in combination. When the four phytochemicals analyzed in FIG. 8 are combined, they act to restrict microbial growth at lower concentrations than any of the chemicals individually acts. The top two panels show the PDA and antimycotic (amphotericin B) controls, while the bottom two panels show PDA supplemented with either 1 mM or 0.3 mM each of indole, nerolidol, linalool and hexenal.

While several ZmPEP3-induced metabolites had antimicrobial activity on their own, we hypothesized that in the plant they would act synergistically to fight microbial growth. Thus in combination, their activity should potentiate one another and together act at a lower concentration than they would individually. Growth medium was supplemented with 1 mM or 0.3 mM each of indole, nerolidol, linalool and hexenal. None of these chemicals was very effective at limiting fungal growth by themselves at these concentrations. However, as shown in FIG. 15, when combined these ZmPEP3-induced chemicals showed much greater limiting effects on fungal growth and sporulation. The bacterial organisms were killed outright by this combination at both concentrations, and for each fungal isolate both growth and sporulation were suppressed.

After ascertaining that these chemical potentiated one another in activity when used in combination, we attempted to produce a mixture more representative of the blend generated by a leaf that had been wounded or wounded and supplied with the ZmPEP3 peptide. Based on the metabolite quantification summarized in FIG. 15 a mix of synthetic chemicals mimicking these proportions was made to represent wounded leaf and ZmPEP3-treated leaf metabolite blend. The formulation of both synthetic mixtures is given in FIG. 14. Both blends were used to supplement growth media and subsequently inoculated with the plant pathogenic organisms.

Figure 16:
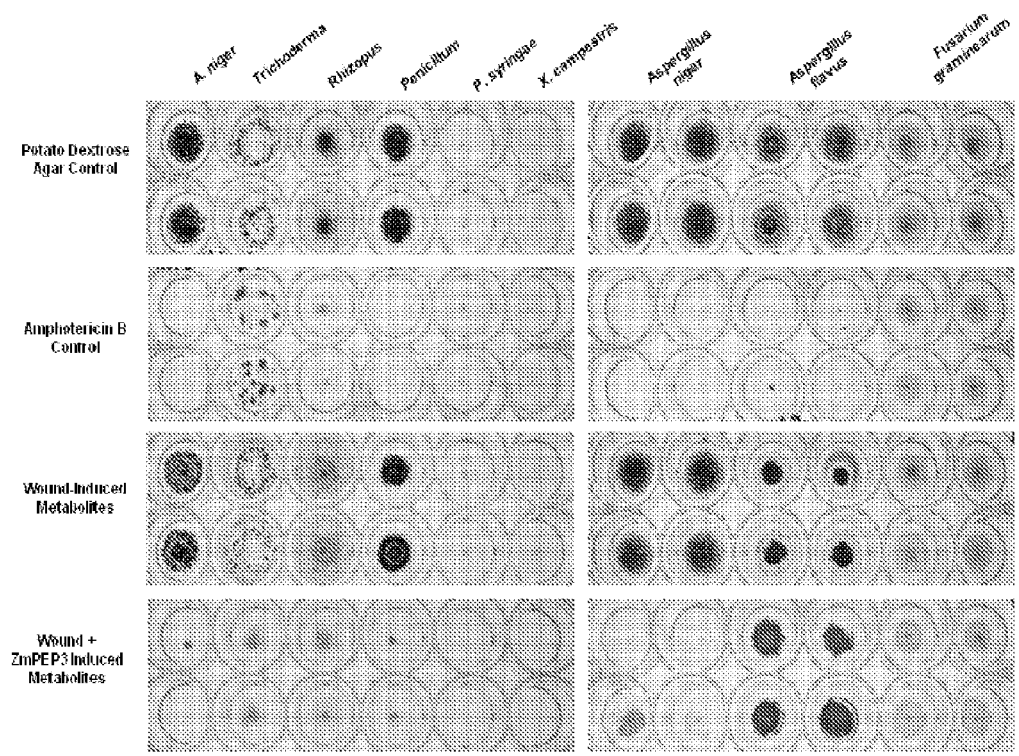
FIG. 16 is a photo of the antimicrobial plate assay using PDA growth medium supplemented with the synthetic maize volatile defense metabolite mixes delineated in Table 5. The top two panels show the PDA and antimycotic (amphotericin B) controls, while the bottom two panels show PDA supplemented with either wound (water)-induced metabolites or ZmPEP3-induced metabolites.

The resulting effects on microbial growth and development are shown in FIG. 16. As shown in the third panel, the wound-induced synthetic blend had no effect on fungal or bacterial growth rates, but did delay sporulation of each fungus. Interestingly, the morphology of a mycotoxin-producing strain of *Aspergillus flavus* was visibly altered, with higher density colonies of a smaller diameter than colonies grown on control medium. The results from growing microorganisms on medium supplemented with the synthetic blend representing chemicals emitted by a ZmPEP3-treated leaf are shown in the fourth (bottom) panel. The ZmPEP3-induced blend killed the bacterial pathogens and strongly suppressed growth of *Aspergillus niger*, *Trichoderma viride*, *Rhizopus* sp. and *Penicillium* sp. Growth of *Aspergillus flavus* and *Fusarium graminearum* was less inhibited by the ZmPEP3 blend, but morphology was significantly changed. *A. flavus* grown on the ZmPEP3 mixture displayed altered colony morphology characterized by filamentous growth and development of pigmentation with sparser sporulation than colonies cultivated on control medium. *F. graminearum* colonies grew on the ZmPEP3 blend, but did not produce the characteristic pink pigmented conidia produced on control medium.

ZmPEP3-Induced Metabolites Suppress Aflatoxin Production by *A. flavus*

The aflatoxins produced by *A. flavus* and secreted into the growth medium are detectable due to green fluorescence they emit under black light (longwave UVA). Fluorescence emission of *A. flavus* colonies growing on the control medium were of visibly greater intensity than that of colonies grown on the medium supplemented with the synthetic blend of ZmPEP3-induced chemicals. This observation was intriguing because fluorescent intensity of the medium surrounding an *A. flavus* colony correlates directly with the concentration of aflatoxin present (Cotty, 1988).

Figure 17:
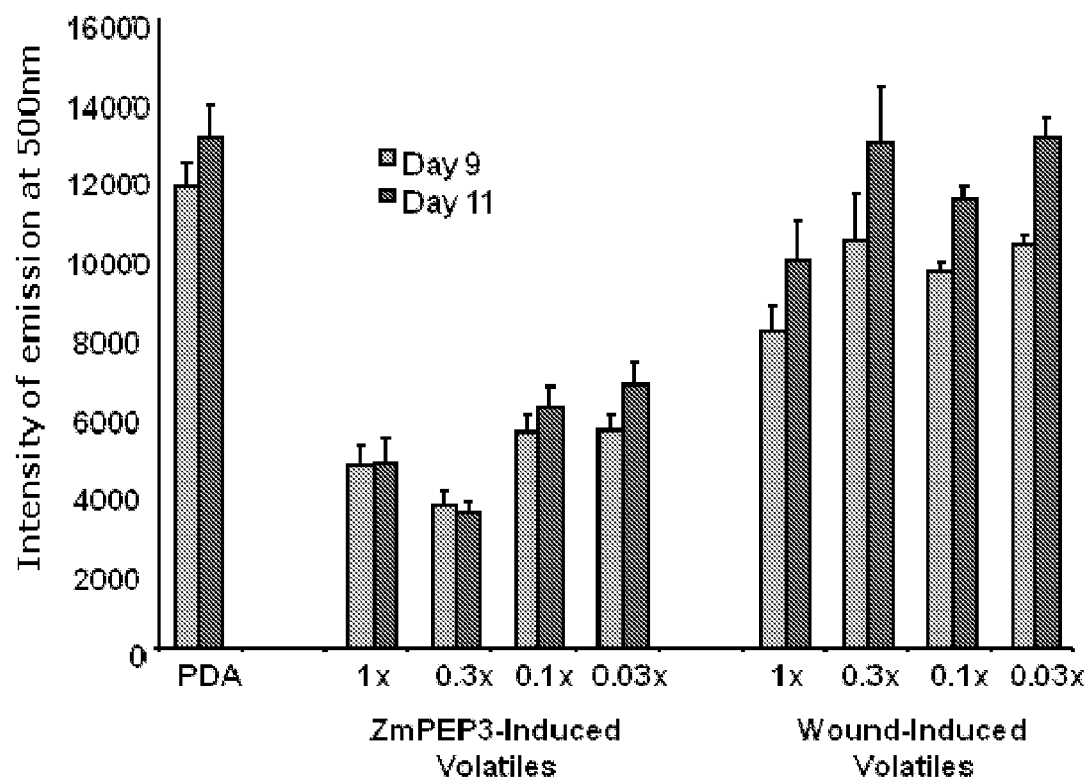
FIG. 17 is a graph of the effects of wound-induced and ZmPEP3-induced defense metabolites on aflatoxin production by *Aspergillus flavus*. Relative amounts of aflatoxin secreted into the growth medium were visualized by fluorescence detection using an excitation wavelength of 390 nm, and a detected emission wavelength of 500 nm. PDA indicates fluorescence detected from *A. flavus* growing on unsupplemented control growth medium, whereas ZmPEP3-induced volatiles and Wound-induced volatiles refer to medium supplemented with the synthetic metabolite blends as formulated in Table 5.
Figure 18:
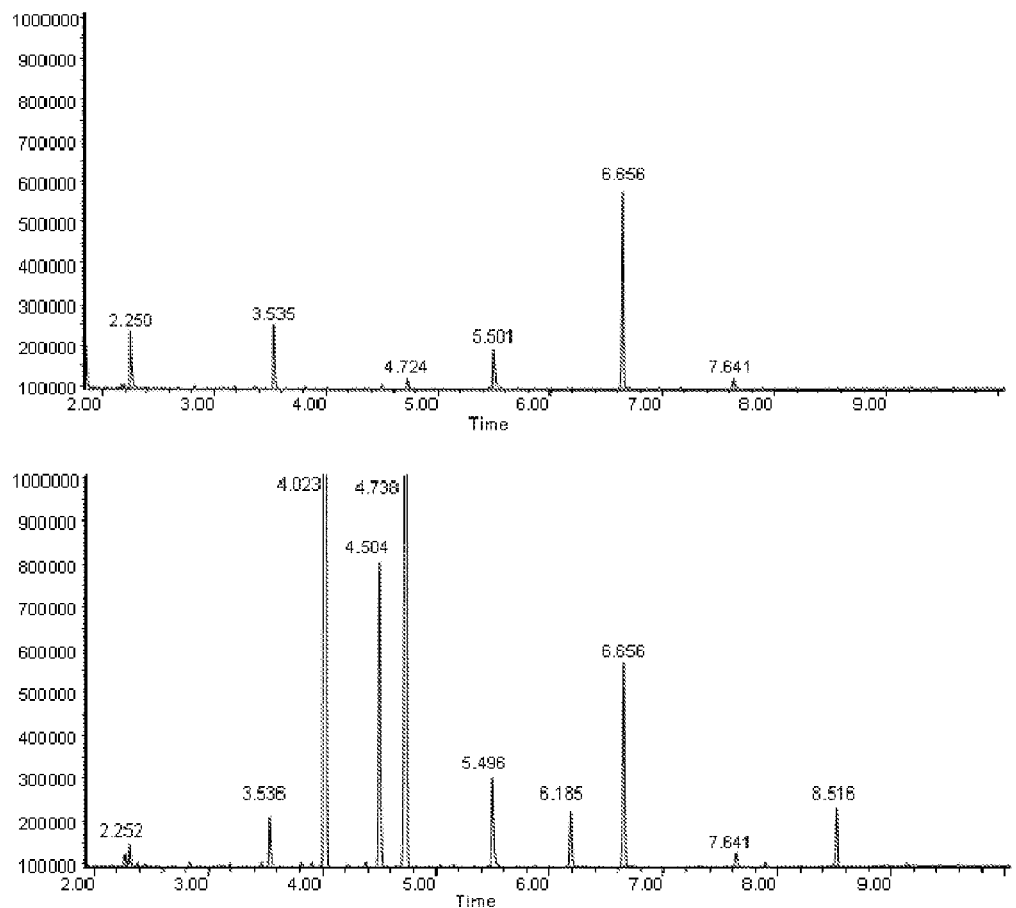
FIG. 18 is a comparative gas chromatogram of the eggplant homolog of ZmPEP3, SmPEP, a bioactive signal activating emission of volatiles from eggplant leaves. Gas chromatograph analysis of volatiles emitted from water-treated eggplant leaves (top) versus SmPEP-treated eggplant leaves (bottom).
Figure 19:
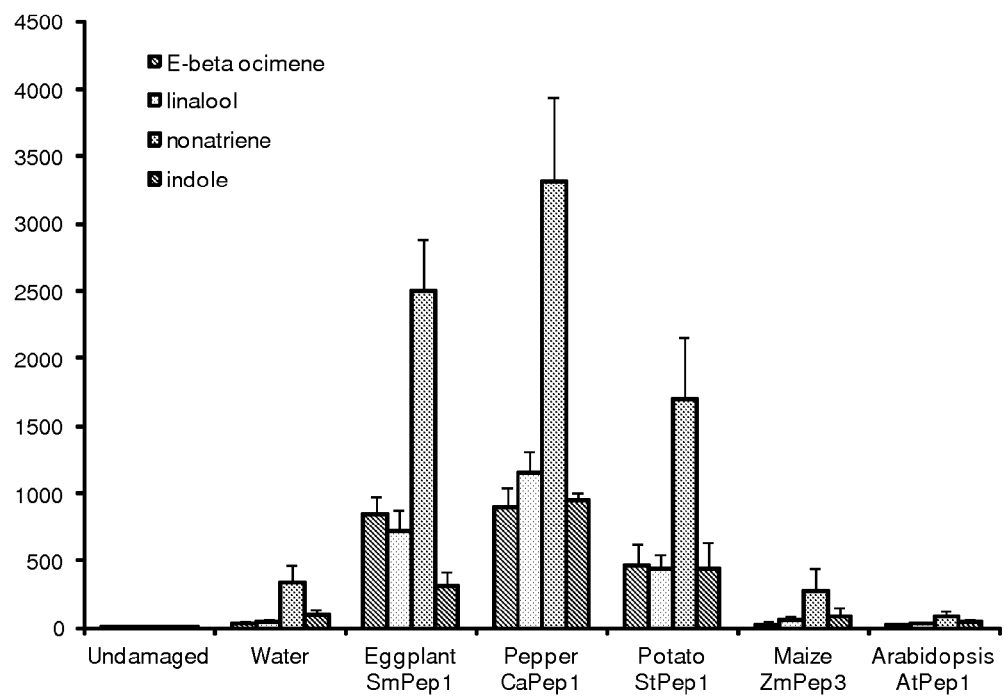
FIG. 19 is a plot of ZmPEP3 homologs from other Solanaceous species which actively signal to induce volatile emissions from eggplant leaves.
Figure 20:
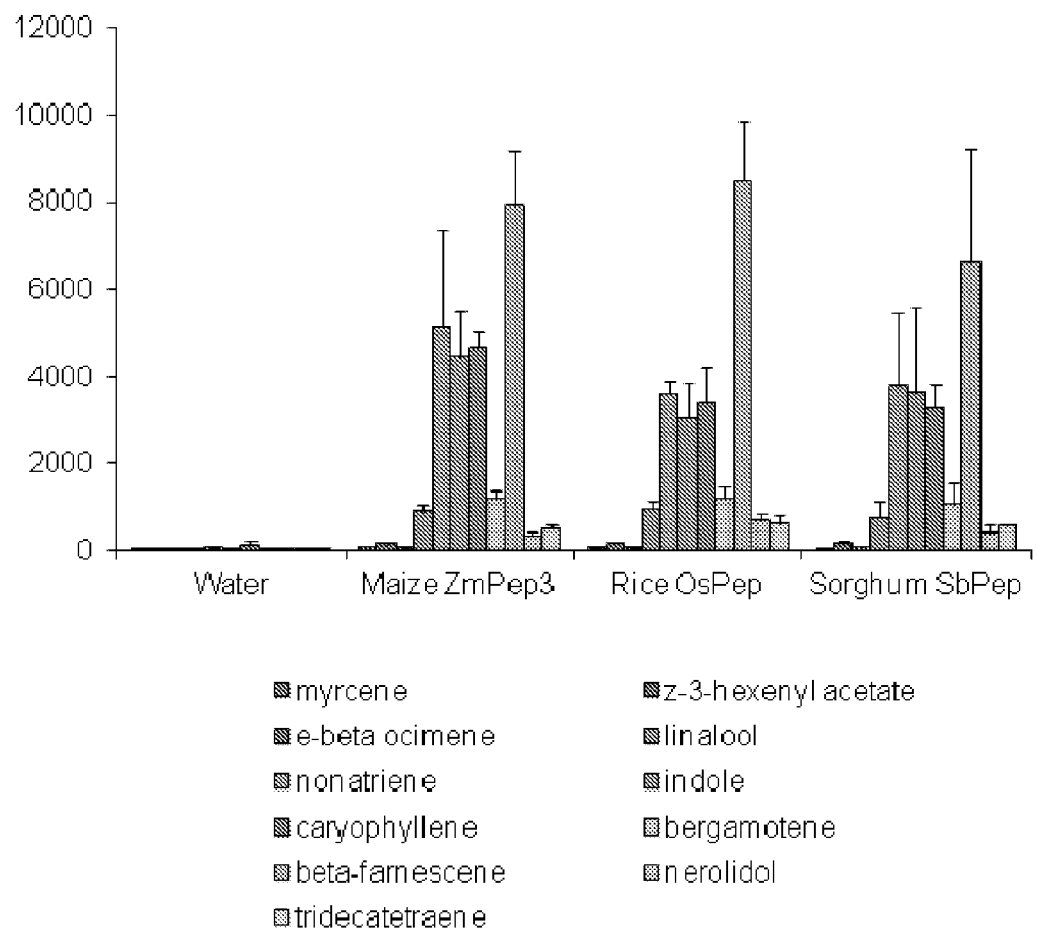
FIG. 20 is a graph of volatiles emitted by maize in response to Peps from related Poaceous species. Homologs of ZmPEP3 from other monocot species are also signals to elicit production of volatile defense metabolites. Quantification of total emitted volatile metabolites collected from excised leaves after a 16 hour treatment with water or with solutions of ZmPEP3 or peptide homologs from monocot crop species rice and sorghum.

An optical scanner was used to detect the emission intensity of the green fluorescence (at 500 nm) upon excitation with 390 nm UVA light. Shown in FIG. 17 is the emission intensity at 500 nm as measured 9 and 11 days post-inoculation for colonies grown on control medium (PDA) versus those grown on medium supplemented with varying concentrations of the synthetic wound-induced or ZmPEP3-induced volatile blends. At the 1× concentration indicated for the ZmPEP3-induced volatiles, the medium was supplemented with the synthetic blend such that each well contained 234 μg/mL indole (2 mM), and all other chemicals were present at proportions equivalent to the recipe shown in FIG. 14. The 1× blend of synthetic wound-induced chemicals also contained each compound at the concentrations delineated in FIG. 14. Each blend was titrated downward at three fold decreasing concentrations as indicated in FIG. 11, such that the lowest concentration of synthetic ZmPEP3-induced mix used to supplement the medium, denoted 0.03×, contained 14.04 μg/mL indole.

Fluorescence emitted by the *A. flavus* colonies on the medium supplemented with the ZmPEP3-induced volatiles was less than half the intensity of those on the control medium (PDA). This was true for all concentrations analyzed at both day 9 and day 11 post-inoculation, indicating that the ZmPEP3-induced volatiles were inhibiting accumulation of aflatoxin in the medium. Green fluorescence detected from *Aspergillus flavus* grown on medium supplemented with the wound-induced volatiles at the highest concentration was moderately reduced compared to the control. Lower concentrations of the wound-induced volatile blend had little effect on aflatoxin concentrations secreted by *A. flavus* as visualized by green fluorescence, indicating that the suppression of aflatoxin accumulation in the medium was an activity particular to the ZmPEP3-induced blend.

ZmPEP3 Induced Volatile Compounds

Production of volatile compounds can play an important role in the attraction of pollinating insects in the process of reproduction and for a successful and high yield seed set. Alternatively, plants can also produce volatile compounds in their reproductive or vegetative parts that attract pest insects or their predators. In this process the volatile profile determines the sensitivity or resistance against harmful organisms such as pest insects, nematodes or fungi. Volatiles are also important for the Flavour and Fragrance, Food and Cosmetics industries that, in a number of cases, produce natural volatile compounds from flowers, herbs, fruits and spices as a source of flavour and fragrance ingredients for usages in perfumes, foods and cosmetics.

Modifying volatile synthesis and release is a means to interfere with plant/insect relations and thereby improve reproductive processes or resistances against pest insects. Scent is also an important trait in the horticulture industry. There is a tendency and a general interest to (re)introduce scent into commercial ornamental varieties. This can be achieved by traditional breeding; however, this requires a lot of time and efforts.

Peptide induced volatility using ZmPEP3 and homologs thereof is therefore and embodiment of the invention. ZMPep maize plant elicitor peptides are set forth in Table [7]3.

TABLE 3

| Maize Plant Elicitor Peptides | |
|---|---|
| ZmPep 1 (SEQ ID NO 1) | VRRRPTTPGRPREGSGGNGGNHH (SEQ ID NO: 1) |
| ZmPep 2 (SEQ ID NO 2) | RRPRPRPPDHAREGSGGNGGVHH (SEQ ID NO: 2) |
| ZmPep 3 (SEQ ID NO 3) | TRTPPWPPCPPEEGSGGNGGSHN (SEQ ID NO: 3) |
| ZmPep 4 (SEQ ID NO 4) | LMRGPAPPGHPAEGAGGRGGSIH (SEQ ID NO: 4) |
| ZmPep 5 (SEQ ID NO 5) | RARGPTPPGLPAEGSGGNGGTKH (SEQ ID NO: 5) |

Volatiles emitted by maize leaves treated with maize Plant Homologs of ZmPEP3 from other plant species were also discovered to have activity as elicitors of volatile emission. As shown in FIG. 20, Peptide homologs from rice and sorghum were capable of activating volatile emissions in maize leaves upon a 16 hour treatment. Furthermore, a peptide homolog from eggplant induced volatile emissions from eggplant leaves. FIG. 18 is a GC trace of volatiles emitted from eggplant leaves treated with water versus those treated with the eggplant peptide homolog SmPEP. Peptide homologs from the related Solanaceous species pepper and potato also induced eggplant volatile emissions, whereas ZmPEP3 and an *Arabidopsis* homolog did not (FIG. 19). This indicates that homologs of ZmPEP3 may be used to manipulate volatile emissions in a variety of species, but peptide bioactivity is limited to target species or those that are within the same plant family.

ZmPep3 is Comparable to an Herbivore-Derived Elicitor in Stimulating Indirect Defense Responses Induced terpene production is vital to anti-herbivore defenses in many plant species (Unsicker et al., Curr Opin Plant Biol. 12:479, 2009; Tholl, Curr Opin Plant Biol. 9:297, 2006; Keeling and Bohlmann, New Phytol 170:657, 2006). Gln-18:3 is among the strongest known elicitors of herbivory-induced maize volatile terpene emissions, and ZmPep3 displays similar or greater activity when applied to leaves at equivalent molar concentrations (Pare et al., Proc Natl Acad Sci USA 95:13971, 1998). Both strongly activate expression of genes encoding Terpene Synthases (TPS) 10 and 23, enzymes for biosynthesis of α-bergamotene and E-β-caryophyllene production respectively (Schnee et al., Proc Natl Acad Sci USA. 103:1129, 2006; Köllner et al., Plant Cell 20: 482, 2008. Although there was no significant quantitative difference in terpenes emitted by leaves treated with ZmPep3 versus Gln-18:3, TPS10 and TPS23 gene expression was more strongly induced by the peptide. These results correspond to significantly greater accumulation of terpenes associated with volatile emission in ZmPep3-treated leaves when internal pools were measured prior to volatile collection.

Shikimate pathway-derived volatile components, including anthranilate and indole increased in leaves following ZmPep3 and Gln18-3 treatment; however, the peptide caused significantly greater accumulation. Indole emission also increased above damage alone in ZmPep3-treated, but not Gln-18:3-treated leaves. Expression of genes encoding the relevant biosynthetic enzymes, Anthranilic Acid Methyl Transferase 1 (AAMT1) and Indole-Glycerol Phosphate Lyase (IGL) were induced by both peptide and the insect elicitor (F; Köllner et al., Plant Physiol 153:1795, 2010; Frey et al., Proc Natl Acad Sci USA. 97:14801, 2000).

ZmPep3 Promotes Accumulation of Transcripts and Metabolites Associated with Direct Defenses Against Herbivores A microarray analysis of transcript levels in leaves that were treated for 12 h with either water or ZmPep3 was employed to better characterize the breadth of ZmPep3-regulated responses. The most highly upregulated probe set in ZmPep3-treated leaves corresponded to the Bowman-Birk type proteinase inhibitor SerPIN. Two additional Bowman-Birk type PIN genes, including Wound Induced Protein 1 (WIP1), were also among the most induced probe sets. Analysis by qRT-PCR validated that both SerPIN and WIP1 were highly expressed in leaves treated with ZmPep3 and to a lesser degree, with Gln-18:3 PINs inhibit insect digestive enzymes and result in reduced larval growth and the discovery that PINs accumulate in response to herbivory contributed to the paradigm of rapidly inducible defenses in plants (Green and Ryan, Science 175:776, 1972; Ryan, Bioessays 10:20, 1989). The assay that identified systemin as a signal regulating tomato defenses was based upon induced PIN accumulation (Pearce et al., Science. 253:895, 1991). Although this herbivore-induced response is conserved across many plant families, regulation of PIN transcription by endogenous plant peptides had not been observed previously outside of the Solanaceae.

In addition to proteinaceous defenses, maize benzoxazinoids contribute to direct defenses against both herbivores and pathogens (Niemeyer, J Agric Food Chem 57:1677, 2009). Indole is produced by the indole glycerol lyase BX1 (Benzoxazine-deficient 1) and modified by a series of cytochrome P450 enzymes (BX2-BXS, Frey et al., Science 277: 696, 1997). The microarray probe sets corresponding to BX1 and BX2 were upregulated by ZmPep3 treatment, and qRT-PCR confirmed that both genes were expressed in response to ZmPep3 or Gln-18:3 12 h post-treatment. This BX gene expression corresponds with increased accumulation of a single benzoxazinoid, 2-hydroxy-4,7-dimethoxy-1,4-benzoxazin-3-one glucoside (HDMBOA-Glc), a highly reactive analog that is also induced by treatment with ZmPep1, JA or biotic attack (FIG. 2H; Oikawa et al., Phytochemistry. 56:669, 2001; Huffaker et al., Plant Physiol. 155:1325, 2011). It was observed recently that intact BX1 function is not required for HDMBOA-Glc accumulation, with IGL being the suspected supplier of indole (Huffaker et al., Plant Physiol 154:2082, 2011). It is hypothesized that simultaneous activation of both IGL and BX1 by ZmPep3 results in increased flux through the benzoxazinoid pathway to produce HDMBOA-Glc.

ZmPep3-Induced Responses are Effective for Both Indirect and Direct Herbivore Defense ZmPep3 elicits the same spectrum of volatile components as S. exigua herbivory, indicating that peptide-treated leaves may also be attractive to entomoparasitic wasps. The generalist parasitoid Cotesia marginiventris attacks many Lepidopteran species including S. exigua and is attracted to herbivory-induced maize volatiles (Turlings et al., Science 250: 1251, 1990). Precisely which components are attractive has been difficult to determine, and the wasps respond strongly to unidentified minor components when subjected to gas chromatograph-coupled electroantennography (Gouinguene et al., J Chem Ecol. 31:1023, 2005). To determine whether the ZmPep3-induced blend was attractive to naïve C. marginiventris, olfactometer assays were conducted with leaves pretreated with ZmPep3, Gln-18:3 or water for 16 h. To ensure that any preference was due to elicited plant responses and not to an inherent attraction or repellence to any treatment substance, leaves treated at time of assay were used as controls. C. marginiventris did not display a statistically significant preference for leaves pretreated with water or Gln-18:3 In contrast, the wasps strongly preferred ZmPep3-pretreated leaves as compared to leaves supplied with ZmPep3 at time of assay. Furthermore, more wasps were attracted to leaves pretreated with ZmPep3 than leaves pretreated with water, showing that attractive volatiles were induced by the peptide. Thus, ZmPep3-regulated responses are sufficient to generate effective indirect defenses against Lepidopteran herbivores.

To assess the role of ZmPep3-induced direct defenses, S. exigua growth on peptide-pretreated leaves was evaluated. Compared to individuals supplied with untreated or water-treated leaves, second instar larvae displayed 40% less biomass gain on ZmPep3-treated leaves. This effect was expected given the potency of ZmPep3-induced proteins and benzoxazinoids against herbivores.

Materials and Methods

Plant and Microbial Materials

Maize varieties used for cloning of the ZmPROPEP precursor gene were Z mays var. B73 and a Z. mays var. Golden Queen, a locally grown sweet corn variety. Both were potted in professional grower's soil mix (Piedmont Pacific, Statham, Ga.) blended with 14-14-14 Osmocote (Scotts, Marysville, Ohio). Both varieties were cultivated in a greenhouse under the following conditions: 12 hour photoperiod, with a minimum of 300 $\mu mol^{-2} s^{-1}$ of photosynthetically active radiation supplied by supplemental lighting. Relative humidity was maintained at 70% and temperature cycled between 24° C. at night and 28° C. during the day.

Fungal isolates representing the following species were cultured from germinating maize seed; Aspergillus flavus, Aspergillus niger, Fusarium graminearum, Trichoderma viride, Penicillium sp. and Rhizopus sp. Each specimen was streaked on ½× potato dextrose agar (PDA) and subcultured until pure isolates were obtained. Organisms were identified through macroscopic colony appearance, examination of morphology under both dissecting and light microscopes, and by PCR analysis of fungal DNA with species-specific primers. Spore suspensions of each isolate were prepared in 30% glycerol and stored at −80° C. For each bioassay, an aliquot of glycerol stock was used to generate a fresh working culture on ½×PDA that was incubated for one week in the dark at 26° C.

Xanthomonas campestris pv. vesicatoria (Xcv) and Pseudomonas syringae pv. tomato DC3000 (Pst) were obtained from Dr. Harry Klee (University of Florida) and initial cultures were aliquoted into 10 µL glycerol stocks and stored at −80° C. For each assay, a fresh working culture was prepared by streaking glycerol stock onto either low salt LB (Pst) or NYGA (Xcv) supplemented with 100 mg/L rifampicin and incubating in the dark at 28° C. for two days.

Peptide and Precursor Gene Identification

The previously identified putative ZmproPep1 peptide precursor sequence (Huffaker et al., Proc Natl Acad Sci USA. 103:10098, 2006) was used to query GenBank registered genomic sequences from Zea mays through the National Center for Biotechnology Information (NCBI) TBLASTN version 2.2.7 algorithm (Altschul, et al., Nucleic Acids Res 25: 3389, 1997). Alignments with the ZmproPEP1 sequence revealed a Gen Bank accession, AC209428, a fragment of chromosome 2 that when translated contained a predicted protein sequence similar to ZmproPEP1 encoded from position 145,897 to 146,424 in the sequence given. The program ProtParam (Gasteiger et al., The Proteomics Protocols Handbook, John M. Walker (ed), Humana Press, 2005), available at ExPASy, was used to predict the probable molecular weight and theoretical pI of the putative precursor protein and active peptide. To determine possible localization of the protein in the cell, several predictive programs were employed, including pSORT (Nakai and Kanehisa, Proteins. 11:95, 1991), TargetP (Emanuelsson et al., J. Mol. Biol. 300:1005, 2000), ChloroP (Emanuelsson et al., Protein Science, 8:978, 1999) and MitoProt (Claros and Vincens, Eur. J. Biochem. 241:779, 1996). Splice sites within the gene were predicted with the program SplicePredictor (Brendel et al., J. Mol. Biol. 276: 85, 1998). The protein secondary structure prediction programs SSpro version 2.0 (Pollastri et al., Bioinformatics, 17 suppl 1:S234, 2001) and SSpro8 (Baldi et al., Bioinformatics. 15:937, 1999) were used to predict secondary structural motifs in the precursor protein.

Peptide Synthesis

A 23 amino acid peptide corresponding to the predicted ZmPep3 active peptide sequence, TRTPPWPPCPPEEGSG-GNGGSHN (SEQ ID NO: 3), was synthesized by solid-phase peptide synthesis at the Protein Core Chemistry Facility (University of Florida, Gainesville) using N-(9-fluorenylmethoxycarbonyl)-protected amino acids on an 432A Peptide Synthesizer (Applied Biosystems). The peptide was cleaved from the resin with modified reagent K, and HPLC-purified on a RP-C18 column with using an water:acetonitrile gradient in 0.1% trifluoroacetic acid. The peptide was confirmed to be of the expected molecular weight by mass spectrometry.

Genomic DNA Isolation

DNA was isolated from Z. mays leaves using the genomic DNA isolation reagent DNAzol (Invitrogen, Carlsbad Calif.). Leaves were ground to fine powder in liquid nitrogen and approximately 100 mg of frozen leaf material was suspended in DNAzol reagent in a 1.5 mL centrifuge tube. The DNA isolation process proceeded as per the instructions provided with the reagent. DNA was resolublized by adding 70 µL Tris-EDTA buffer (pH 8.0); yields were determined by measuring the $A_{260}$ of the solutions, and then aliquots were stored at −20° C.

Cloning of ZmproPEP3 Gene

Primers were designed to amplify a 532 base pair region of chromosome 2 containing the genomic sequence encoding ZmproPEP3. The forward primer sequence was 5' GCTTG- TACATTCCGGTTCGT 3' (SEQ ID NO: 6) and the reverse primer sequence was 5' ACCGGAGAAGGCTAGAGAGG 3' (SEQ ID NO: 7). Using a template of 1 µg genomic DNA from either B73 or Golden Queen variety, reactions were assembled using 1 unit of AccuPrime Taq in 10× AccuPrime PCR buffer II (Invitrogen, Carlsbad Calif.) to give a final $Mg^{2+}$ concentration of 2 mM and a final dNTP concentration of 200 µM per nucleotide. The primer concentration used was 200 nM for each primer. Each reaction was run using the following amplification program: An initial 3 minutes at 94° C., followed by a denaturing step of 30 seconds at 94° C., an annealing step of 30 seconds at 55° C., and an elongation step of 1.5 minutes at 72° C. After 35 replicates of this cycle, a final elongation step of 10 minutes at 72° C. was employed. The products were visualized by analyzing a 15 µL aliquot diluted with 2 µL DNA blue/orange loading dye (Promega Biosciences Inc., San Luis Obispo Calif.) on a 1% agarose/Tris-Acetate-EDTA gel impregnated with ethidium bromide. A 100 bp DNA step ladder (Promega Biosciences Inc., San Luis Obispo Calif.) was employed for calibration.

For both Golden Queen and B73 varieties, the genomic PCR reaction produced only one visible band between 500 and 600 base pairs in length. This fragment was cloned into the pCR2.1-TOPO vector using a TOPO-TA cloning kit (Invitrogen, Carlsbad Calif.) as per kit instructions. Cloning reactions were transformed into TOP10F' chemically competent *E. coli* by heat shocking the cells in a 42° C. water bath for thirty seconds (Invitrogen, Carlsbad Calif.). Following transformation, the transformed cells were plated on Luria-Bertani plates containing 50 µg/mL kanamycin as a selection agent. The inoculated plates were incubated overnight at 37° C., after which colonies were screened for an insert of the appropriate size (532 base pairs) using the primers specific to ZmproPEP3 described above. Colonies that appeared to contain the ZmproPEP3 genomic insert were used to inoculate 4 mL liquid cultures (in LB broth with 50 µg/mL kanamycin). After an overnight incubation, the plasmids carrying the cloned ZmproPEP3 insert were isolated from the liquid cultures using a QIAGEN Plasmid Mini kit (QIAGEN Inc., Valencia, Calif.) as per the kit instructions. The isolated plasmid DNA for each clone was quantified by measuring the $A_{260}$, and stored at −20° C.

Each plasmid sample was sequenced using ABI Prism BigDye terminator (Applied Biosystems, Foster City Calif.) sequencing reaction mixture containing buffer, AmpliTaq DNA polymerase polymerase and fluorescent BigDye terminator nucleotides. As a template for the reaction 750 ng plasmid DNA was used along with 3.2 pmol of either the M13 Forward or M13 Reverse vector primers supplied with the TOPO-TA cloning kit (Invitrogen Corporation, Carlsbad, Calif.). Both a forward and a reverse sequencing reaction were performed. Each reaction was run using the following amplification program: An initial 3 minutes at 95° C., followed by 35 replicates of this cycle: 20 seconds at 95° C., 60 seconds at 50° C., and 4 min at 60° C. After, a final elongation step of 10 minutes at 72° C. was employed. All sequencing reactions were analyzed at the ICBR DNA Sequencing Core Facility (University of Florida Gainesville, Fla.).

Excised Leaf Bioassay of ZmPEP3 Activity

Leaves of three week old maize plants were excised and placed in four mL glass vials containing 3 mL of either milliQ water or 5 µM ZmPep3 in milliQ water. For each treatment and time point three leaves of leaf stage five were assayed. Time course assays began at 5 PM and at the time points indicated, material was harvested for RNA and metabolite analysis. Midribs were removed from the leaves and each was separately frozen immediately in liquid nitrogen for later RNA & metabolite analysis. For examination of induced volatile compounds, intact leaves were collected at 9 AM the following morning (16 hours post-treatment).

RNA Isolation

Maize tissues that had been harvested and frozen in liquid nitrogen were ground to a fine powder using a porcelain mortar and pestle. Approximately 100 mg of frozen powdered plant material was transferred to a 2 mL microcentrifuge tubes to which 1 mL of Trizol reagent (Invitrogen, Carlsbad Calif.) was added. RNA isolation was performed as per the Trizol instructions, supplemented by an acid:phenol:chloroform partitioning step to minimize contaminating DNA. RNA was solublized in 50 µL diethylpyrocarbonate (DEPC)-treated water. RNA yield was quantified by measuring the $A_{260}$, and the samples were stored at −20° C.

Semi-Quantitative RT-PCR

RNA was reverse transcribed using all components from the RETROscript kit (Ambion, Austin Tex.). The 20 µL reverse transcription reactions were assembled as per kit instructions The reverse transcription reaction was allowed to proceed for one hour at 44° C., followed by a ten minute incubation at 92° C.

Semi-quantitative RT-PCR reactions were assembled as follows: 1.2 µL of the cDNA generated in the reverse transcription reactions was used as template for 25 µL PCR reactions. Each reaction contained Platinum 10×PCR buffer (Invitrogen, Carlsbad Calif.) and the final concentration of $Mg^{2+}$ and dNTPs were 1.5 mM and 200 µM, respectively. Platinum Taq polymerase (Invitrogen, Carlsbad Calif.) was added at 0.5 units per reaction, while primers were used at 0.4 µM each. All primers were designed to for an annealing temperature of 56° C., to amplify a product of 250 to 350 base pairs and to span introns when possible. The ZmActin1 gene transcript (GenBank# J01238) has been described in the literature as an effective housekeeping control transcript for the study of maize defense gene expression (Erb et al., 2009), and was therefore used to permit comparisons of relative transcript abundance from sample to sample. Genes to be analyzed for responsiveness to ZmPep3 were all shown in previous work to be associated with either pathogen or herbivore resistance (Erb et al., Plant J 59: 292, 2009; Doehlemann et al., Plant J. 56:181, 2008; Köliner et al., Plant Cell 20: 482, 2008; Chen et al., Phytopathology 94:938, 2004; Chen et al., Phytopathology 97:1094, 2007; Schnee et al., Plant Physiol 130: 2049, 2002; Frey et al., Proc Natl Acad Sci USA. 97:14801, 2000).

Semiquantitative RT-PCR requires that the amplification reaction product for any particular transcript be analyzed during the exponential phase of transcript amplification. Genes with higher basal expression levels require fewer amplification cycles to be detected, whereas low abundance transcripts require more. The optimal cycling time for each gene such that detection of an amplified transcript would occur during the exponential phase was determined by investigating the primers for each marker gene in reactions running from 25 to 37 amplification cycles. The cycling time for each transcript studied is indicated in Table 1. PCR reactions followed this amplification program: An initial denaturing/polymerase activating step of 3 minutes at 94° C., followed by repetitions of the following three steps: a thirty second denaturation phase at 94° C., a thirty second annealing period at 56° C., and a one minute elongation step at 72° C. For each transcript the optimal number of amplification cycles was programmed as given in Table 1, and the program was terminated with a ten minute final 72° C. elongation phase.

A 20 µL aliquot of each reaction product was diluted with 2 µL DNA blue/orange loading dye (Promega Biosciences Inc., San Luis Obispo Calif.) and analyzed electrophoretically on a 1% agarose/Tris-Acetate-EDTA gel impregnated with ethidium bromide alongside a 100 bp DNA step ladder (Promega Biosciences Inc., San Luis Obispo Calif.). The gel was visualized on a Gel Doc XR Imaging System (BioRad, Hercules, Calif.) using Quantity One version 4.6.2 software (BioRad, Hercules, Calif.). A high resolution image of the gel was captured on the Et/Br setting using the transilluminator, and was analyzed using the Quantity One program (BioRad, Hercules, Calif.). The greater the band intensity observed, the more transcript was initially present in the sample analyzed.

Volatile Collection and Analysis

Volatiles were collected by a previously described method (Schmelz et al., Planta. 214:171, 2001). Briefly, excised leaves were placed in glass cylinders (Analytical Research Systems, Gainesville, Fla., USA) and maintained under their original lighting conditions. Clean, humidified air was passed through the cylinders (550 ml/min) and the leaf-emitted volatiles were trapped on 50 mg Super Q (80/100 mesh; Alltech, Deerfield, Ill., USA) for 30 minutes. Super Q traps were eluted with 150 µl methylene chloride with 400 ng of nonyl acetate added as an internal standard. At least three leaf replicates were used for each treatment.

Volatiles were analyzed by gas chromatography-mass spectrometry (GC-MS) using an Agilent (Agilent Technologies, Inc., Santa Clara, Calif.) 7890A gas chromatograph (carrier gas; He at 1.2 ml min$^{-1}$; splitless injector, temperature 220° C., injection volume 1 µl) with an DB-1MS column (100% Dimethylpolysiloxane; 15 m long, 250 µm i.d., 0.1 µm film thickness). Temperatures were programmed from 40° C. (0.5 min hold) at 12° C. min$^{-1}$ to 180° C. then 220° C. (2.0 min hold for the post run). Signals were captured with a flame ionization detector (250° C.). The GC was coupled to an HP 5973 quadrupole-type mass selective detector with transfer line, source, and quadrupole temperatures of 230° C., 230° C. and 150° C., respectively. Ions were generated at a 70 eV potential and scanned at a range of 30-500 amu. Volatile compounds were identified by comparison of retention times with authentic standards and by comparison of mass spectra with Wiley and NIST libraries.

Assay of ZmPEP3-Induced Metabolites for Antimicrobial Activity:

Antimicrobial assays were performed in 24 well tissue culture plates with 0.5 mL aliquots of ½× potato dextrose agar (PDA) growth media in each well. Control wells contained unsupplemented ½×PDA. Experimental wells contained ½×PDA supplemented by chemicals to be analyzed. ½×PDA was autoclaved and then separated into 10 mL aliquots in 15 mL conical tubes that were incubated at 60 degrees. Each chemical to be analyzed was added to an aliquot of ½×PDA and vortexed to mix. Immediately after mixing, the ½×PDA mixture was plated out before the media solidified. All plates were covered immediately after pouring to minimize volatile compound escape. Plates were allowed to cool, and then a sterile pasteur pipette with a bulb was used to create wells in the center of each well.

Fresh cultures of fungal and bacterial plant pathogens were generated as described above. For each organism, liquid suspensions were made by flooding the plate with a solution of sterile 0.1% Triton x-100 (Sigma-Aldrich, St. Louis, Mo.). Density of bacterial populations was quantified via measurements of $A_{600}$, whereas density of fungal spore suspensions was quantified through spore density counts under a light microscope aided by a hemocytometer. All organisms were adjusted to a density of $1 \times 10^4$ cells/spores per mL and 5 µL of each suspension were pipetted into the center of each well. Plates were sealed with three layers of parafilm, observed and photographed for one week.

Assay of ZmPEP3-Induced Metabolites for Effects on Aflatoxin Production:

Aflatoxins produced by *Aspergillus flavus* are secreted into the growth medium. These toxin molecules absorb UV light and fluoresce; aflatoxin $B_1$ and $B_2$ emit blue light whereas aflatoxin $G_1$ and $G_2$ molecules green (Hara et al., App Microbiol., 27:1118, 1974; Cotty, Appl. Environ. Microbiol. 54:274, 1988). The intensity of the fluorescence detected in growth media directly correlates to the amount of aflatoxin present, with higher emission intensity indicating a greater concentration of toxin (Cotty, Appl. Environ. Microbiol. 54:274, 1988). Green fluorescence was observed to emanate from the media surrounding the *A. flavus* colonies grown for antimicrobial assays when they were examined under UV light (372 nm). This fluorescence was measured using a Bio Tek Synergy4 multimode microplate reader (Bio Tek Instruments, Inc., Winooski, Vt.). The optical detectors were set to read fluorescence from the bottom of the 24 well plates, and a scan of optimal excitation and detected emission wavelengths was performed. The optimal UV wavelength for excitation for our conditions was found to be 390 nm (longwave UVA), whereas the optimal wavelength to detect green fluorescence emission was 500 nm. Each plate was scanned for intensity of green fluorescence, with wells that had no fungus growing in them used to determine baseline fluorescence. For each treatment four replicates were analyzed.

What is claimed is:

1. A composition comprising the isolated peptide of SEQ ID NO. 3, said composition has herbivory and volatile defense signal peptide activity.

2. The composition of claim 1 comprising a biologically acceptable carrier.

3. An isolated polynucleotide comprising
   comprising a nucleotide sequence that encodes SEQ ID N0:3, wherein the nucleotide sequence is operably linked to a heterologous promoter sequence.

4. A cell comprising the isolated polynucleotide of claim 3.

5. The cell of claim 4 selected from the group consisting of a plant cell, a bacterial cell, a fungal cell and an insect cell.

6. The cell of claim 5 which is a plant cell.

7. A plant comprising the cell of claim 6.

8. The plant of claim 7, said plant is from the family Poaceae.

9. The plant of claim 8, selected from the group consisting of maize, wheat, sorghum, millets, rice, rye, oats, bamboo, sugarcane, annual bluegrass, annual meadowgrass, *Poa annua*, orchardgrass, *Festuca* spp., sudangrass, ryegrass, Indiangrass, Bermudagrass, bentgrass, reeds and switchgrass.

10. The plant of claim 9 that exhibits increased herbivory, emission of volatiles and enhanced resistance to pathogens as compared to a plant lacking the polynucleotide.

11. The plant of claim 10 wherein the pathogens are selected from the group consisting of *Aspergillus niger, Trichoderma viride, Rhizopus* sp., *Penicillium* sp., *Aspergillus flavus* and *Fusarium graminearum*.

* * * * *

SEQUENCE LISTING

```
<160> NUMBER OF SEQ ID NOS: 13

<210> SEQ ID NO 1
<211> LENGTH: 23
<212> TYPE: PRT
<213> ORGANISM: Zea mays

<400> SEQUENCE: 1

Val Arg Arg Arg Pro Thr Thr Pro Gly Arg Pro Arg Glu Gly Ser Gly
1               5                   10                  15

Gly Asn Gly Gly Asn His His
            20

<210> SEQ ID NO 2
<211> LENGTH: 23
<212> TYPE: PRT
```

```
<213> ORGANISM: Zea mays

<400> SEQUENCE: 2

Arg Arg Pro Arg Pro Arg Pro Pro Asp His Ala Arg Glu Gly Ser Gly
1               5                   10                  15

Gly Asn Gly Gly Val His His
            20

<210> SEQ ID NO 3
<211> LENGTH: 23
<212> TYPE: PRT
<213> ORGANISM: Zea mays

<400> SEQUENCE: 3

Thr Arg Thr Pro Pro Trp Pro Pro Cys Pro Pro Glu Glu Gly Ser Gly
1               5                   10                  15

Gly Asn Gly Gly Ser His Asn
            20

<210> SEQ ID NO 4
<211> LENGTH: 23
<212> TYPE: PRT
<213> ORGANISM: Zea mays

<400> SEQUENCE: 4

Leu Met Arg Gly Pro Ala Pro Pro Gly His Pro Ala Glu Gly Ala Gly
1               5                   10                  15

Gly Arg Gly Gly Ser Ile His
            20

<210> SEQ ID NO 5
<211> LENGTH: 23
<212> TYPE: PRT
<213> ORGANISM: Zea mays

<400> SEQUENCE: 5

Arg Ala Arg Gly Pro Thr Pro Pro Gly Leu Pro Ala Glu Gly Ser Gly
1               5                   10                  15

Gly Asn Gly Gly Thr Lys His
            20

<210> SEQ ID NO 6
<211> LENGTH: 20
<212> TYPE: PRT
<213> ORGANISM: Zea mays

<400> SEQUENCE: 6

Gly Cys Thr Thr Gly Thr Ala Cys Ala Thr Thr Cys Cys Gly Gly Thr
1               5                   10                  15

Thr Cys Gly Thr
            20

<210> SEQ ID NO 7
<211> LENGTH: 20
<212> TYPE: PRT
<213> ORGANISM: Zea mays

<400> SEQUENCE: 7

Ala Cys Cys Gly Gly Ala Gly Ala Ala Gly Gly Cys Thr Ala Gly Ala
1               5                   10                  15

Gly Ala Gly Gly
            20
```

```
<210> SEQ ID NO 8
<211> LENGTH: 108
<212> TYPE: PRT
<213> ORGANISM: Zea mays

<400> SEQUENCE: 8

Met Ala Glu Val Glu Ala Ser Ala Pro Leu Phe Ala His Pro Phe Ser
1               5                   10                  15

Leu Leu Gln Pro Leu Leu Arg Ala Cys Ala Gly Cys Leu Val Gly Leu
            20                  25                  30

His Gly Tyr Cys Ser Asp Asn Asn Asp Ser Lys Pro Ala Ala Ala Ala
        35                  40                  45

Ile Ala Glu Ser Ser Thr Pro Gln Glu Gly Glu Ala Gly Gly Gly Gly
50                  55                  60

Asp Asp Asp Asp Lys Ala Ala Tyr Leu Tyr Val Gln Glu Val Ala
65                  70                  75                  80

Thr Pro Val Leu Ala Ala Arg Arg Pro Thr Gln Pro Gly Pro Pro
                85                  90                  95

Glu Glu Gly Ser Gly Gly His Gly Gly Ser His Asn
            100                 105

<210> SEQ ID NO 9
<211> LENGTH: 118
<212> TYPE: PRT
<213> ORGANISM: Zea mays

<400> SEQUENCE: 9

Val Val Glu Glu Gln Ala Ser Ala Pro Leu Gln Leu Leu Arg Ala
1               5                   10                  15

Cys Ala Gly Cys Leu Val Gly Leu Leu Arg Gly Tyr Arg Ser Asp Pro
            20                  25                  30

Lys Pro Ala Ala Ala Ala Ala Ala Ser Val Ala Ala Glu Ser Pro
        35                  40                  45

Gln Glu Gly Asp Lys Pro Phe Gly Ser Val Ser Val Arg Gly His Arg
50                  55                  60

Leu Ile Ile Ser Pro Cys Cys Asn Pro Met Asp Val Gln Pro Leu Arg
65                  70                  75                  80

Cys Leu Tyr Val Gln Glu Val Gly Thr Gln Val Leu Ala Ala Thr
                85                  90                  95

Arg Thr Pro Pro Trp Pro Pro Cys Pro Pro Glu Glu Gly Ser Gly Gly
            100                 105                 110

Asn Gly Gly Ser His Asn
            115

<210> SEQ ID NO 10
<211> LENGTH: 147
<212> TYPE: PRT
<213> ORGANISM: Zea mays

<400> SEQUENCE: 10

Met Asp Gln Arg Val Ser Gln Glu Ser Ser Asp Arg Arg Arg Lys
1               5                   10                  15

Arg Lys Asp Val Ala Ala Ala Val Pro Glu Gly Val His Gly Glu Ser
            20                  25                  30

Thr Asp Asn Gly Gly Tyr Asp Asp Thr Asp Glu Thr Ala Gly Val Leu
        35                  40                  45
```

```
Thr Lys Glu Gln Gln Ala Val Asp Val Val Glu Glu Gln Ala Ser Ala
     50                  55                  60

Pro Leu Gln Leu Leu Arg Ala Cys Ala Gly Cys Leu Val Gly Leu
 65                  70                  75                  80

Leu Arg Gly Tyr Arg Ser Asp Pro Lys Pro Ala Ala Ala Ala Ala
                 85                  90                  95

Ala Ser Val Ala Ala Glu Ser Pro Gln Glu Gly Asp Lys Pro Phe Gly
            100                 105                 110

Ser Glu Glu Val Gly Thr Gln Val Leu Ala Ala Thr Arg Thr Pro
            115                 120                 125

Pro Trp Pro Pro Cys Pro Pro Glu Glu Gly Ser Gly Gly Asn Gly Gly
    130                 135                 140

Ser His Asn
145

<210> SEQ ID NO 11
<211> LENGTH: 146
<212> TYPE: PRT
<213> ORGANISM: Zea mays

<400> SEQUENCE: 11

Met Asp Gln Arg Val Ser Gln Glu Ser Ser Asp Arg Arg Arg Lys
 1               5                  10                  15

Arg Lys Asp Val Ala Ala Ala Val Ser Glu Gly Val His Gly Glu Ser
            20                  25                  30

Thr Asp Asn Gly Gly Tyr Asp Asp Thr Asp Glu Thr Ala Gly Val Leu
            35                  40                  45

Thr Lys Glu Gln Gln Ala Val Asp Val Val Glu Glu Gln Ala Ser Ala
     50                  55                  60

Pro Leu Gln Leu Leu Arg Ala Cys Ala Gly Cys Leu Val Gly Leu
 65                  70                  75                  80

Leu His Gly Tyr Arg Ser Asp Pro Lys Pro Ala Ala Ala Ala Ala
                 85                  90                  95

Ala Ser Val Ala Ala Glu Ser Pro Gln Glu Gly Asp Lys Pro Phe Gly
            100                 105                 110

Ser Glu Glu Val Gly Thr Gln Val Leu Ala Ala Thr Arg Thr Pro Pro
            115                 120                 125

Trp Pro Pro Cys Pro Pro Glu Glu Gly Ser Gly Gly Asn Gly Gly Ser
    130                 135                 140

His Asn
145

<210> SEQ ID NO 12
<211> LENGTH: 146
<212> TYPE: PRT
<213> ORGANISM: Zea mays

<400> SEQUENCE: 12

Met Asp Gln Arg Val Ser Gln Glu Ser Ser Asp Arg Arg Arg Lys
 1               5                  10                  15

Arg Lys Asp Val Ala Ala Ala Val Pro Glu Gly Val His Gly Glu Ser
            20                  25                  30

Thr Asp Asn Gly Gly Tyr Asp Asp Thr Asp Glu Thr Ala Gly Val Leu
            35                  40                  45

Thr Lys Glu Gln Gln Ala Val Asp Val Val Glu Glu Gln Ala Ser Ala
     50                  55                  60
```

-continued

```
Pro Leu Gln Leu Leu Leu Arg Ala Cys Ala Gly Cys Leu Val Gly Leu
 65                  70                  75                  80

Leu Arg Gly Tyr Arg Ser Asp Pro Lys Pro Ala Ala Ala Ala Ala Ala
                 85                  90                  95

Ala Ser Val Ala Ala Glu Ser Pro Gln Glu Gly Asp Lys Pro Phe Gly
                100                 105                 110

Ser Glu Glu Val Gly Thr Gln Val Leu Ala Ala Thr Arg Thr Pro Pro
            115                 120                 125

Trp Pro Pro Cys Pro Pro Glu Glu Gly Ser Gly Gly Asn Gly Gly Ser
        130                 135                 140

His Asn
145

<210> SEQ ID NO 13
<211> LENGTH: 145
<212> TYPE: PRT
<213> ORGANISM: Zea mays

<400> SEQUENCE: 13

Met Asp Gln Arg Val Ser Gln Glu Ser Ser Ser Asp Arg Arg Arg Lys
  1               5                  10                  15

Arg Lys Asp Val Ala Ala Ala Val Pro Glu Gly Val His Gly Glu Ser
                 20                  25                  30

Thr Asp Asn Gly Gly Tyr Asp Asp Thr Asp Glu Thr Ala Gly Val Leu
             35                  40                  45

Thr Lys Glu Gln Gln Ala Ala Asp Val Val Glu Glu Glu Ala Ser Ser
         50                  55                  60

Pro Leu Gln Leu Leu Leu Arg Ala Cys Ala Gly Cys Leu Val Gly Leu
 65                  70                  75                  80

Leu Cys Gly Tyr Arg Ser Asp Pro Lys Pro Ala Ala Ala Ala Ala Ala
                 85                  90                  95

Ser Val Ala Ala Glu Ser Pro Gln Glu Gly Asp Lys Pro Phe Gly Ser
                100                 105                 110

Glu Glu Val Gly Thr Gln Val Leu Ala Ala Thr Arg Thr Pro Pro Trp
            115                 120                 125

Pro Pro Cys Pro Pro Glu Glu Gly Ser Gly Gly Asn Gly Gly Ser His
        130                 135                 140

Asn
145
```